(12) United States Patent
Jenson et al.

(10) Patent No.: US 7,686,783 B2
(45) Date of Patent: Mar. 30, 2010

(54) PERFUSION AND EMBOLIC PROTECTION

(75) Inventors: Mark L. Jenson, Greenfield, MN (US);
William J. Drasler, Minnetonka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 101 days.

(21) Appl. No.: 11/693,956

(22) Filed: Mar. 30, 2007

(65) Prior Publication Data
US 2008/0243066 A1    Oct. 2, 2008

(51) Int. Cl.
*A61M 29/00*    (2006.01)

(52) U.S. Cl. .................... 604/104; 604/96.01; 606/200

(58) Field of Classification Search ............. 604/96.01, 604/99.01, 101.01, 101.04, 103, 103.04–103.09, 604/104; 606/192, 194, 200
See application file for complete search history.

(56) References Cited

U.S. PATENT DOCUMENTS

| | | | |
|---|---|---|---|
| 4,406,656 A | 9/1983 | Hattler et al. |
| 4,425,908 A | 1/1984 | Simon |
| 4,601,713 A | 7/1986 | Fuqua |
| 4,710,181 A | 12/1987 | Fuqua |
| 4,738,666 A | 4/1988 | Fuqua |
| 5,106,368 A | 4/1992 | Uldall et al. |
| 5,180,364 A | 1/1993 | Ginsburg |
| 5,320,605 A | 6/1994 | Sahota |
| 5,421,832 A | 6/1995 | Lefebvre |
| 5,472,418 A | 12/1995 | Palestrant |
| 5,474,537 A | 12/1995 | Solar |
| 5,573,508 A | 11/1996 | Thornton |
| 5,735,831 A | 4/1998 | Johnson et al. |
| 5,738,667 A | 4/1998 | Solar |
| 5,795,322 A | 8/1998 | Boudewijn |
| 5,810,874 A | 9/1998 | Lefebvre |
| 5,814,064 A | 9/1998 | Daniel et al. |
| 5,827,324 A | 10/1998 | Cassell et al. |
| 5,947,995 A | 9/1999 | Samuels |
| 6,001,118 A | 12/1999 | Daniel et al. |
| 6,129,739 A | 10/2000 | Khosravi |

(Continued)

FOREIGN PATENT DOCUMENTS

WO    00/12169    3/2000

(Continued)

*Primary Examiner*—Kevin C. Sirmons
*Assistant Examiner*—Bhisma Mehta
(74) *Attorney, Agent, or Firm*—Crompton, Seager & Tufte LLC

(57) ABSTRACT

Disclosed is a combination perfusion and occlusion device that can have a perfusion member, an occlusive member and an elongate member. The perfusion member can be an elongate perfusion member that can have a collapsed configuration and an expanded configuration. In the collapsed configuration, the perfusion member can be disposed around the elongate member. In the expanded configuration, the perfusion member can define a perfusion lumen. The occlusive member can have a collapsed configuration and an expanded configuration. The occlusive member in the collapsed configuration can have a low profile that can facilitate insertion of the occlusive member in a body lumen. In the expanded configuration the occlusive member can be a structure that restricts the flow of fluids through a body vessel, for example a filter or another structure that restricts the flow of fluids. The occlusive member can be disposed on the elongate member, for example on a distal portion of the elongate member.

34 Claims, 20 Drawing Sheets

U.S. PATENT DOCUMENTS

| | | |
|---|---|---|
| 6,152,946 A | 11/2000 | Broome et al. |
| 6,168,579 B1 | 1/2001 | Tsugita |
| 6,179,859 B1 | 1/2001 | Bates et al. |
| 6,179,861 B1 | 1/2001 | Khosravi et al. |
| 6,183,492 B1 | 2/2001 | Hart et al. |
| 6,190,357 B1 | 2/2001 | Ferrari et al. |
| 6,245,087 B1 | 6/2001 | Addis |
| 6,277,138 B1 | 8/2001 | Levinson et al. |
| 6,277,139 B1 | 8/2001 | Levinson et al. |
| 6,290,710 B1 | 9/2001 | Cryer et al. |
| 6,336,934 B1 | 1/2002 | Gilson et al. |
| 6,361,545 B1 | 3/2002 | Macoviak et al. |
| 6,371,971 B1 | 4/2002 | Tsugita et al. |
| 6,395,014 B1 | 5/2002 | Macoviak et al. |
| 6,398,756 B2 | 6/2002 | Peterson et al. |
| 6,425,909 B1 | 7/2002 | Dieck et al. |
| 6,527,746 B1 | 3/2003 | Oslund et al. |
| 6,530,939 B1 | 3/2003 | Hopkins et al. |
| 6,537,294 B1 | 3/2003 | Boyle et al. |
| 6,544,279 B1 | 4/2003 | Hopkins et al. |
| 6,589,263 B1 | 7/2003 | Hopkins et al. |
| 6,595,967 B2 | 7/2003 | Kramer |
| 6,605,074 B2 | 8/2003 | Zadno-Azizi et al. |
| 6,645,224 B2 | 11/2003 | Gilson et al. |
| 6,740,061 B1 | 5/2004 | Oslund et al. |
| 6,936,059 B2 | 8/2005 | Belef |
| 6,939,361 B1 | 9/2005 | Kleshinski |
| 6,951,555 B1 | 10/2005 | Suresh et al. |
| 6,969,396 B2 | 11/2005 | Krolik et al. |
| 7,014,647 B2 | 3/2006 | Brady et al. |
| 2002/0095174 A1 | 7/2002 | Tsugita et al. |
| 2003/0233115 A1* | 12/2003 | Eversull et al. ............ 606/194 |
| 2004/0193207 A1 | 9/2004 | Boismier |
| 2004/0220521 A1 | 11/2004 | Barbut |
| 2004/0249409 A1 | 12/2004 | Krolik et al. |
| 2005/0101987 A1 | 5/2005 | Salahieh |
| 2005/0131449 A1 | 6/2005 | Salahieh |
| 2005/0288631 A1 | 12/2005 | Lewis et al. |
| 2006/0195138 A1 | 8/2006 | Goll et al. |

FOREIGN PATENT DOCUMENTS

| | | |
|---|---|---|
| WO | 03/090834 | 11/2003 |

* cited by examiner

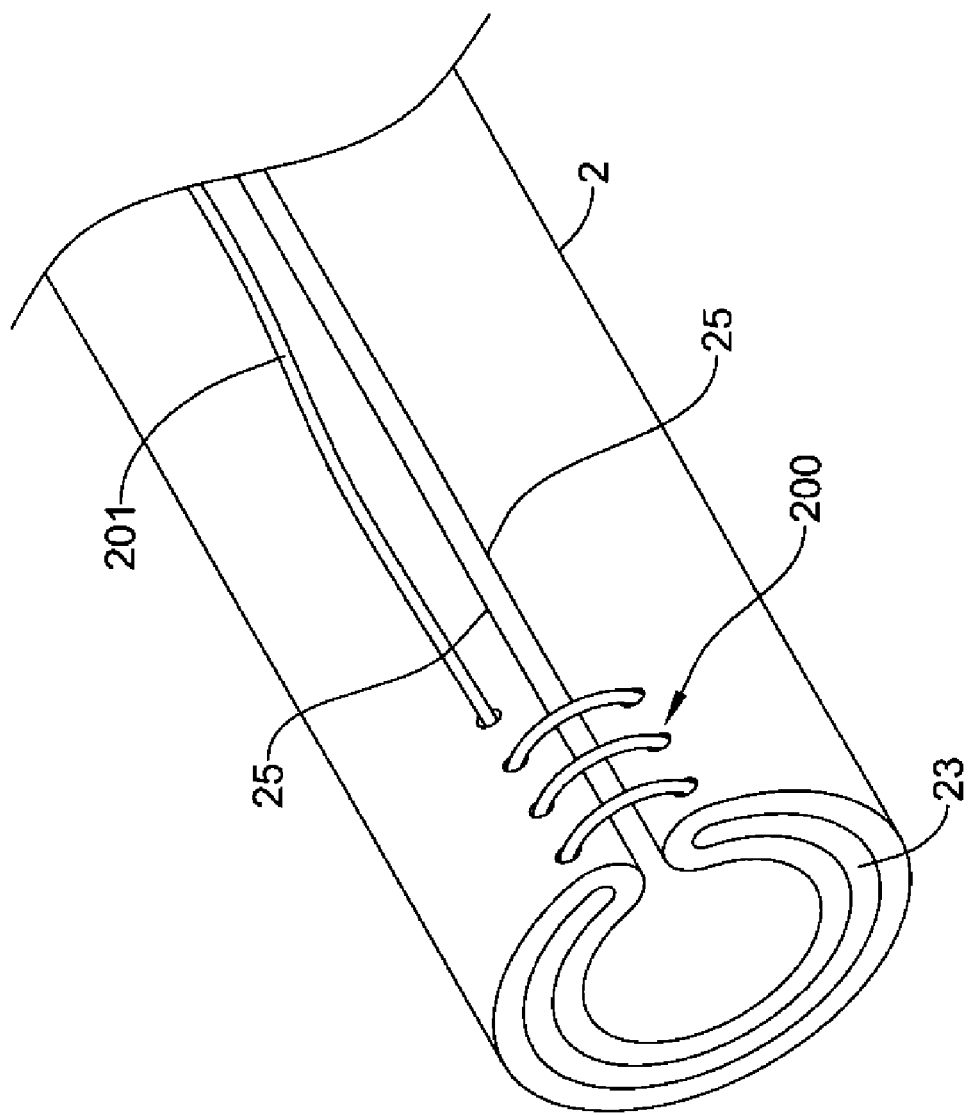

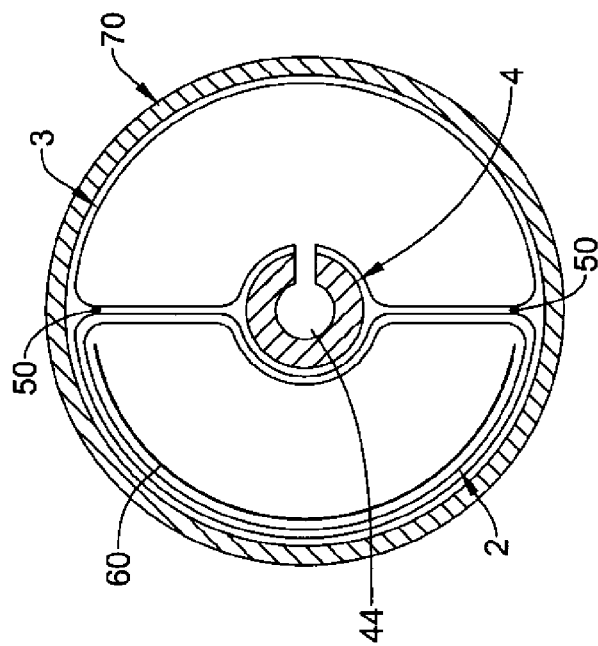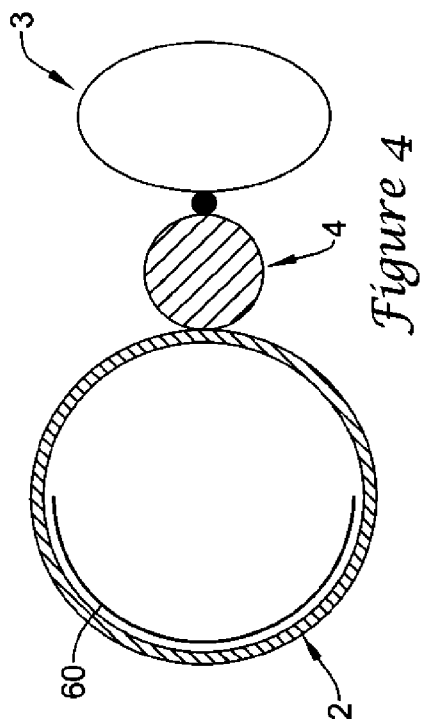

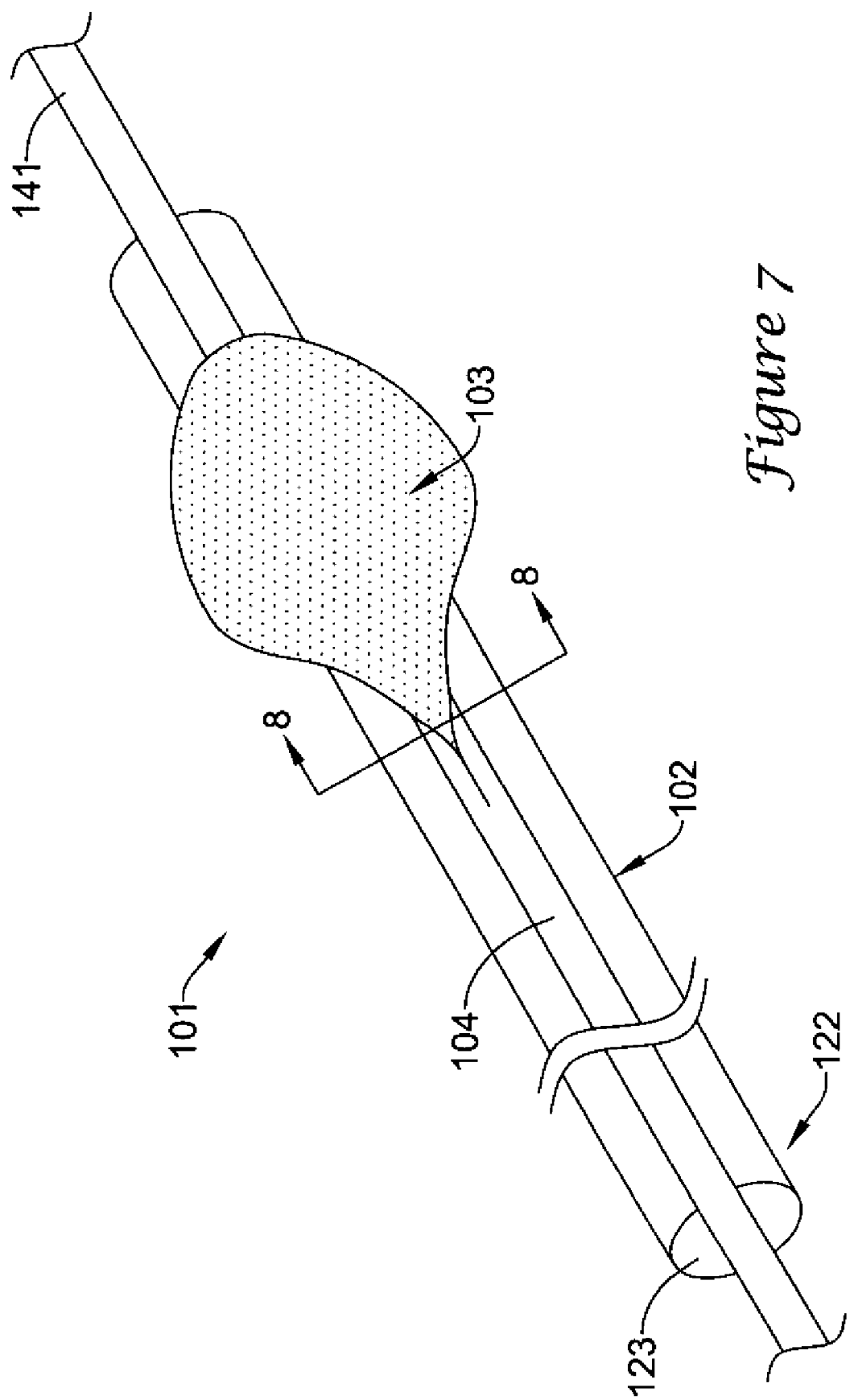

PERFUSION AND EMBOLIC PROTECTION

RELATED APPLICATIONS

This application is related to U.S. application Ser. No. 11/693,795, entitled "PERFUSION DEVICE," filed on Mar. 30, 2007, and herein incorporated by reference in its entirety.

TECHNICAL FIELD

The invention pertains generally to the design and use of perfusion and embolic protection devices.

BACKGROUND

Blockages within the vasculature can cause a variety of adverse conditions with the human body. Such blockages can be caused by blood clots or other emboli or deposits on vessel walls. Medical devices, such as emboli capturing devices, exist to address these issues. Embolic protection devices can be, for example, an occlusion balloon or other type of occluder which substantially restricts passage of debris past the balloon, but which also substantially restricts passage of blood, medications, or other materials past the occlusion balloon or other occluder. Occlusion devices can be used, for example, to isolate an area of vasculature in order to perform a procedure such as removal of emboli. Embolic protection devices can also be a filter type device, for example a filter which collects any debris which is too large to pass through the filter. The filter can become clogged with debris or with thrombus and can thereby become partially or entirely occlusive over time, thus restricting the passage of blood, medications, or other materials past the filter.

Embolic protection devices are sometimes placed downstream from a treatment area in a blood vessel so that emboli produced by any treatment can be captured or contained or otherwise treated. Embolic protection devices can also be placed upstream from a treatment area, or both upstream and downstream to isolate the treatment area. Limitations on the flow of fluids caused by these devices, especially blood, can cause issues such as ischemia in patients, and may limit the effectiveness of any infused medication or other materials as well. A number of different structures and assemblies for such devices and procedures are known, each having certain advantages and disadvantages. However, there is an ongoing need to provide alternative structures, assemblies and methods.

SUMMARY OF SOME EMBODIMENTS

The present disclosure provides several alternative designs, materials and methods of manufacturing and use of alternative medical device structures and assemblies.

Accordingly, an example embodiment can be found in a combination perfusion and occlusion device that comprises an elongate shaft, an occlusive member and a perfusion member. The occlusive member can be disposed on a distal portion of the elongate member, and can have a collapsed configuration and an expanded configuration. The collapsed configuration can provide a low profile in order to facilitate delivery of the device through tortuous vasculature, and the expanded profile can be sized and configured to partially or substantially entirely occlude and restrict flow through all or a portion of a vessel of a patient. The perfusion member can be an elongate member that has a collapsed configuration and an expanded configuration. The collapsed configuration can facilitate delivery of the device through tortuous vasculature and, in its expanded configuration the perfusion member can define a perfusion lumen through which blood and/or other fluids can be perfused. The perfusion member can be disposed along the elongate member, and in its collapsed configuration the perfusion member can be disposed around (e.g., wrapped around) the elongate shaft. Further, either or both of the perfusion member and the occlusive member can be eccentrically disposed about the elongate member when they are in their expanded configurations. The perfusion member can be attached to the elongate member along a portion, or all of, the perfusion member, or the perfusion member and elongate member can be unattached. The perfusion member and the elongate member can also be longitudinally translatable with respect to one another.

In another example embodiment, a method of occluding and perfusing within a body vessel is disclosed. In one step, a combination perfusion and occlusion device can be provided, the device having a perfusion member, an occlusive member and an elongate member. The perfusion, occlusive and elongate members can be advanced, together or in any suitable combination thereof, through a body vessel of a patient, to a point of interest. The occlusive member can be deployed from a collapsed configuration to an expanded configuration. The perfusion member can be deployed from a collapsed configuration to an expanded configuration. Before, after, and/or during occlusion of the body vessel, blood and/or other fluids can be perfused through a perfusion lumen of the perfusion member.

BRIEF DESCRIPTION OF THE FIGURES

FIGS. 2A and 2B show a distal portion of alternative perfusion members;

FIGS. 4, 5, and 5A are cross-sectional views of alternative embodiments or configurations of the device shown in FIG. 3;

FIGS. 6 and 7 are perspective views of alternative embodiments of a combination occlusion and perfusion device in the collapsed and expanded configurations, respectively;

Figure 2:
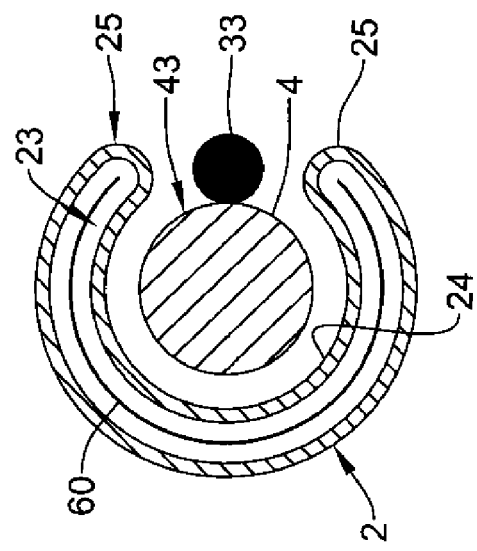
FIG. 2 is a cross-sectional view of a portion of the device shown in FIG. 1.

While the invention is amenable to various modifications and alternative forms, some specifics thereof have been shown by way of example in the drawings and will be described in detail. It should be understood, however, that the intention is not to limit the invention to the particular embodiments described. On the contrary, the intention is to cover all modifications, equivalents, and alternatives failing within the spirit and scope of the invention.

DETAILED DESCRIPTION OF SOME EMBODIMENTS

For the following defined terms, these definitions shall be applied, unless a different definition is given in the claims or elsewhere in this specification.

The term "polymer" will be understood to include polymers, copolymers (e.g., polymers formed using two or more different monomers), oligomers and combinations thereof, as well as polymers, oligomers, or copolymers that can be formed in a miscible blend by, for example, coextrusion or reaction, including transesterification. Both block and random copolymers are included, unless indicated otherwise.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

Figure 1:
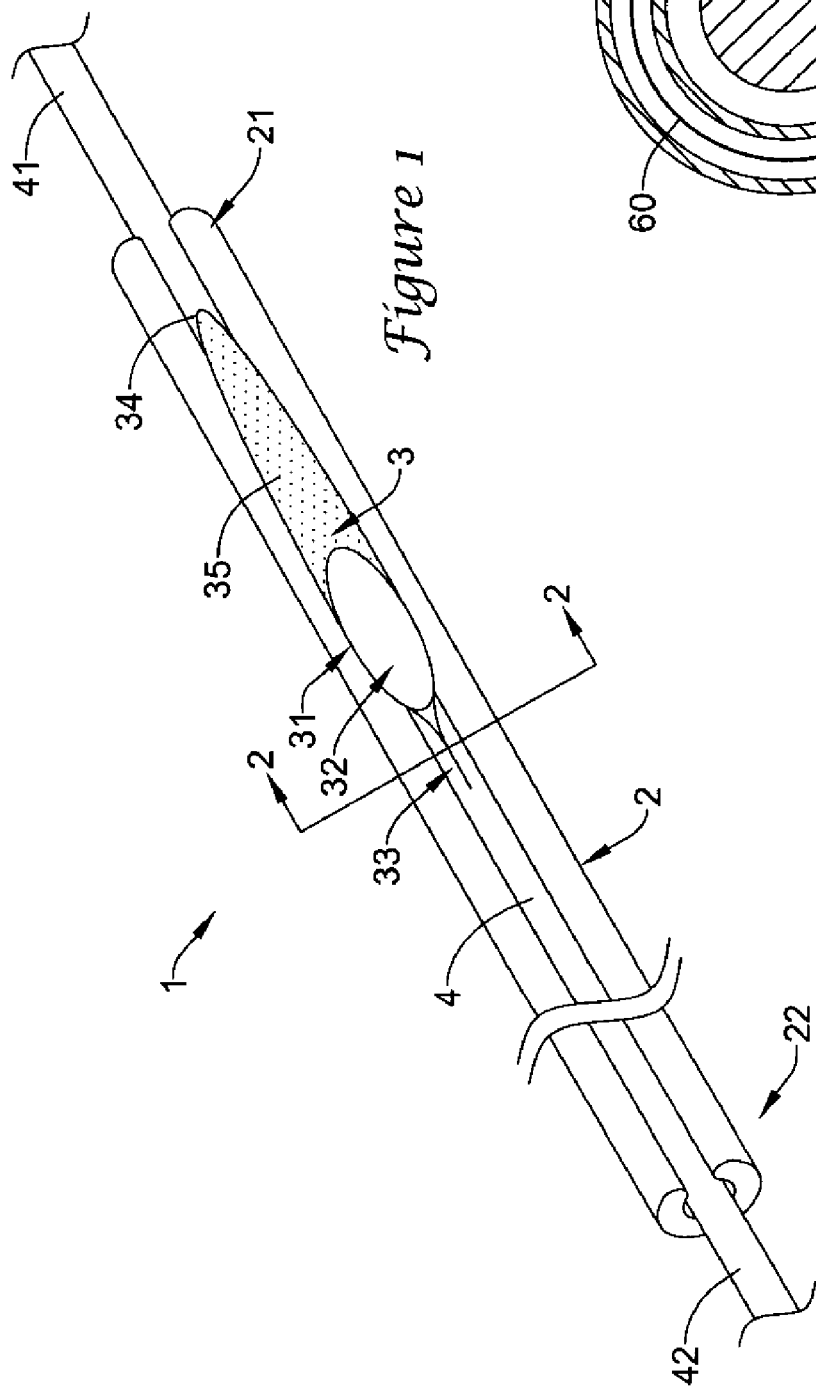
FIG. 1 is a perspective view of an example of a combination perfusion and occlusion device.

Turning to FIG. 1, a perspective view of an example combination occlusion and perfusion device 1 is shown. The device 1 can have a perfusion member 2, an occlusive member 3 and an elongate member 4. The elongate member 4 can be, for example, an elongate shaft such as a guidewire. The elongate member 4 can have a proximal end 42 and a distal end 41 and the perfusion member 2 can have a proximal end 22 and a distal end 21.

Generally, the occlusive member can be an embolic protection device. For example, it can be any suitable type of embolic protection device that restricts the free flow of fluids, for example a filter or an occluder (e.g., a balloon occluder). Further, the word "occlude" as used herein can include the prevention of the free flow of fluids, for example the act of filtering material from a fluid or otherwise blocking the flow of fluids through a vessel.

As shown in the example of FIG. 1, the occlusive member 3 can be a filter. The filter can have a support hoop 31 that can form a filter opening 32. In some embodiments, the support hoop 31 can be directly attached to the elongate member 4. In some cases a proximal extension 33 can extend from the support hoop 31, and this proximal extension 33 can be attached to the elongate member 4 in addition to or instead of attaching the support hoop 31 to the elongate member 4. The filter can also comprise a filter material or occlusive membrane 35. For example, a filter material 35 can extend distally from the support hoop 31, forming a filter basket. The filter material 35 can extend from the support hoop 31 to the filter distal end 34. The filter material 35 could be made of a variety of materials and, if porous, can have a variety of pore sizes. For example, the filter material 35 could have a pore size such that emboli can be filtered from a patient's blood stream. In other cases, the pore size could be reduced or the pores eliminated so that the filter material substantially blocks the flow of blood or other fluids. It is also contemplated that other filter designs can be incorporated into the combination occlusion and perfusion device as the occlusive member 3.

In other embodiments, the occlusive member 3 can comprise any other suitable occlusive member. In some embodiments, an occlusive member 3 could be shaped to block a vessel within a patient, and could be substantially impervious to the flow of blood and/or other bodily fluids. For example, the occlusive member 3 could be entirely impervious to the flow of blood and/or bodily fluids. One such embodiment could be a filter shaped element, for example as described above with respect to FIG. 1, which is substantially impervious to fluid flow such as blood. In yet other embodiments, the occlusive member 3 could be an inflatable occlusive member, for example an occlusive balloon or other occlusive member that has an inflatable portion. The inflatable member or portion can be sized and configured to cause the occlusive member to occlude a body vessel when deployed. The inflatable occlusive member or portion could be in fluid communication with a lumen 44 of the elongate member 4 so that the inflatable occlusive member could be deployed by inflation.

Any of the occlusive members described herein can be placed distal of a region of interest or proximal of a region or interest. Further, the device 1 could also have two or more of any of the above occlusive members, or any combination of the above occlusive members. The two or more occlusive members could be used to isolate a portion of a body vessel, for example in order to perform a procedure on a portion of the vessel. In the case where the device 1 comprises two or more inflatable occlusive members, the inflatable occlusive members could use the same inflation lumen or they could each have separate inflation lumens, for example separate inflation lumens in the elongate member 4.

In some example embodiments, the occlusive member 3 can have multiple configurations, for example a collapsed configuration and an expanded configuration. In the collapsed configuration, the occlusive member 3 can have a relatively low profile compared to the expanded configuration, which can facilitate the movement of the occlusive member 3 through the vasculature of a patient. In the expanded configuration, a cross-section of the occlusive member 3 can substantially or entirely fill a cross-section of a body vessel, for example in order to block emboli from traveling through a patient's vasculature and/or to isolate an area of interest from fluid flow before, after, and/or during an intravascular procedure. In some cases, as discussed below, a cross-section of the occlusive member 3 can substantially (e.g., entirely) occlude a portion of a cross-section of a body vessel that is not blocked by the perfusion member 2. Alternatively, if the perfusion member 2 is not present a cross-section of the occlusive member 3 can substantially (e.g., entirely) occlude the entire cross-section of a body vessel.

The different occlusive member structures that are discussed above can be deployed in a variety of ways. For example, an occlusive member can be predisposed to being in either the expanded or collapsed configuration. In some examples, the occlusive member can be predisposed to assume the expanded configuration, and a structure can be used to hold it in the collapsed configuration until it is desired to deploy the occlusive member. One such structure could be an external sheath that can contain the occlusive member in a collapsed configuration for delivery. In addition, the perfusion member could be sized and configured to wrap around the occlusive member, holding it in a collapsed configuration, for example for delivery of the occlusive member. In addition, in another example, a proximal extension can be attached to a frame of the occlusive member, and the proximal extension can extend proximally to a point where an operator of the device can manipulate the proximal extension. As an example, the proximal extension can extend along side an elongate member or through a lumen of an elongate member. Manipulating the proximal extension can manipulate the occlusive member between collapsed and expanded configurations. As another example, the proximal extension 33 extending from the filter of FIG. 3 could run down a lumen of the elongate member 4.

All or a portion of an occlusive member could also be inflatable, as mentioned above. A structure could have an inflatable cuff or other structure that assists the occlusive member in deploying from a collapsed to an expanded configuration. In addition, the occlusive member could be a balloon that is shaped and configured to occlude all or a portion of a patient's vasculature. In such a case, the inflatable portion of the occlusive member could be fluidly coupled to a source of inflation fluid through one or more inflation lumens, for example inflation lumens defined by the elongate member. Inflation of the inflatable portion of the occlusive member can cause the occlusive member to deploy toward an expanded configuration. Further, in some cases where the occlusive member is predisposed to assume the collapsed configuration, depressurizing the fluid in the inflatable portion can cause the occlusive member to exhaust the fluid within the inflatable portion and assume the collapsed configuration. In other cases, suction can be used to remove fluid from the inflatable portion, causing it to assume the collapsed configuration.

Placement of an occlusive member in an expanded configuration in a body vessel can result in the restriction of blood flow to a portion of a body (for example, if the occlusive member is substantially impervious to fluid flow and/or if the occlusive member is porous and the pores become blocked). If this blood flow is restricted for an extended time, ischemia can occur. Thus, in cases where a filter can become occluded with emboli and/or where an occlusive member is being used to partially or substantially (e.g., entirely) restrict blood flow through a vessel, it may be desirable to perfuse blood around or past the occlusive member.

In FIG. 1, a perfusion member 2 is shown disposed along the elongate member 4. The perfusion member 2 can have a collapsed and an expanded configuration. In FIG. 1, the perfusion member 2 is shown in a collapsed configuration, which can form a relatively low profile compared to an expanded configuration (for example, the expanded configuration of FIG. 3, discussed below). In the embodiment of FIG. 1, the perfusion member 2 is collapsed around the elongate member 4 along a substantial portion of the length of the elongate member 4 from a proximal portion to a distal portion of the elongate member 4. Further, the perfusion member 2, when in a collapsed configuration, can be disposed around the elongate member 4 along the entire length of the perfusion member 2.

Turning to FIG. 2, a cross-section of the perfusion member 2 in its collapsed configuration is shown disposed around the elongate member 4. Further, a portion of the occlusive member 3, for example the proximal extension 33 can be disposed along (e.g., attached to) the elongate member 4. In some embodiments, the perfusion member 2 can be attached to the elongate member 4 at one or more discrete points or along a portion or portions of the length of the elongate member 4. In some cases, the perfusion member 2 can be attached to the elongate member 4 along substantially all of (e.g., the entire) the length of the perfusion member 2. In other embodiments, the perfusion member 2 and the elongate member 4 can be longitudinally translatable with respect to one another. For example, at least a portion of the perfusion member 2 could be disposed around the elongate member 4, and an inner surface 24 of the collapsed perfusion member 2 and an outer surface 43 of the elongate member 4 can be unattached.

In some cases where the perfusion member 2 and the elongate member 4 are longitudinally translatable with respect to one another, the perfusion member 2, when in its collapsed configuration, can be advanced over the elongate member 4. In such a case, the elongate member 4 could be advanced through a patient's vasculature with or without the occlusive member 3 on it, and the perfusion member 2 could then be advanced over the elongate member 4. In addition, the perfusion member 2 could be advanced through a patient's vasculature first and then the elongate member 4, with or without the occlusive member 3 on it, can be passed down along the collapsed perfusion member 2, as shown in the cross-section of FIG. 2. Further, when the perfusion member 2 and the elongate member 4 are longitudinally translatable with respect to one another, adjustments can be made in the positioning of the distal end 21 of the perfusion member 2 with respect to the occlusive member 3, either before or after deploying the perfusion member 2 and/or the occlusive member 3.

In an alternative embodiment, the perfusion member 2, when in its collapsed configuration, can be disposed around the elongate member 4 along only a portion of the length of the perfusion member 2. For example, when the perfusion member 2 is in its collapsed configuration, a distal portion of the perfusion member 2 can be disposed around the elongate member 4. Further, a proximal portion of the perfusion member 2 can be disposed alongside the elongate member 4. In some cases, the perfusion member 2 and the elongate member 4 could be longitudinally translatable with respect to one another. In some embodiments, if a distal portion of the perfusion member 2 is disposed around the elongate member 4 and a proximal portion of the perfusion member 2 is disposed along side the elongate member 4, the perfusion member 2 can be longitudinally translatable with respect to the elongate member 4 in a single operator exchange type fashion. As mentioned above, the perfusion member 2 could also be attached to the elongate member 4.

Further, the perfusion member 2 can comprise a variety of materials. In one embodiment, the perfusion member 2 can made from a material that is elastic in at least a radial direction about an axis running the length of the perfusion member 2. With the perfusion member 2 being an elastic member, it can form different size lumens and/or accommodate different flow rates by expanding to allow for higher flow rates. In other embodiments, the perfusion member 2 can be inelastic in a radial direction about an axis running the length of the perfusion member 2, which can ensure that it will not expand beyond a certain size when it deploys. In such a case, the perfusion member 2 may be sized for a certain application. One of ordinary skill in the art would recognize the instances when either or both of these types of designs would be suitable.

Figure 3:
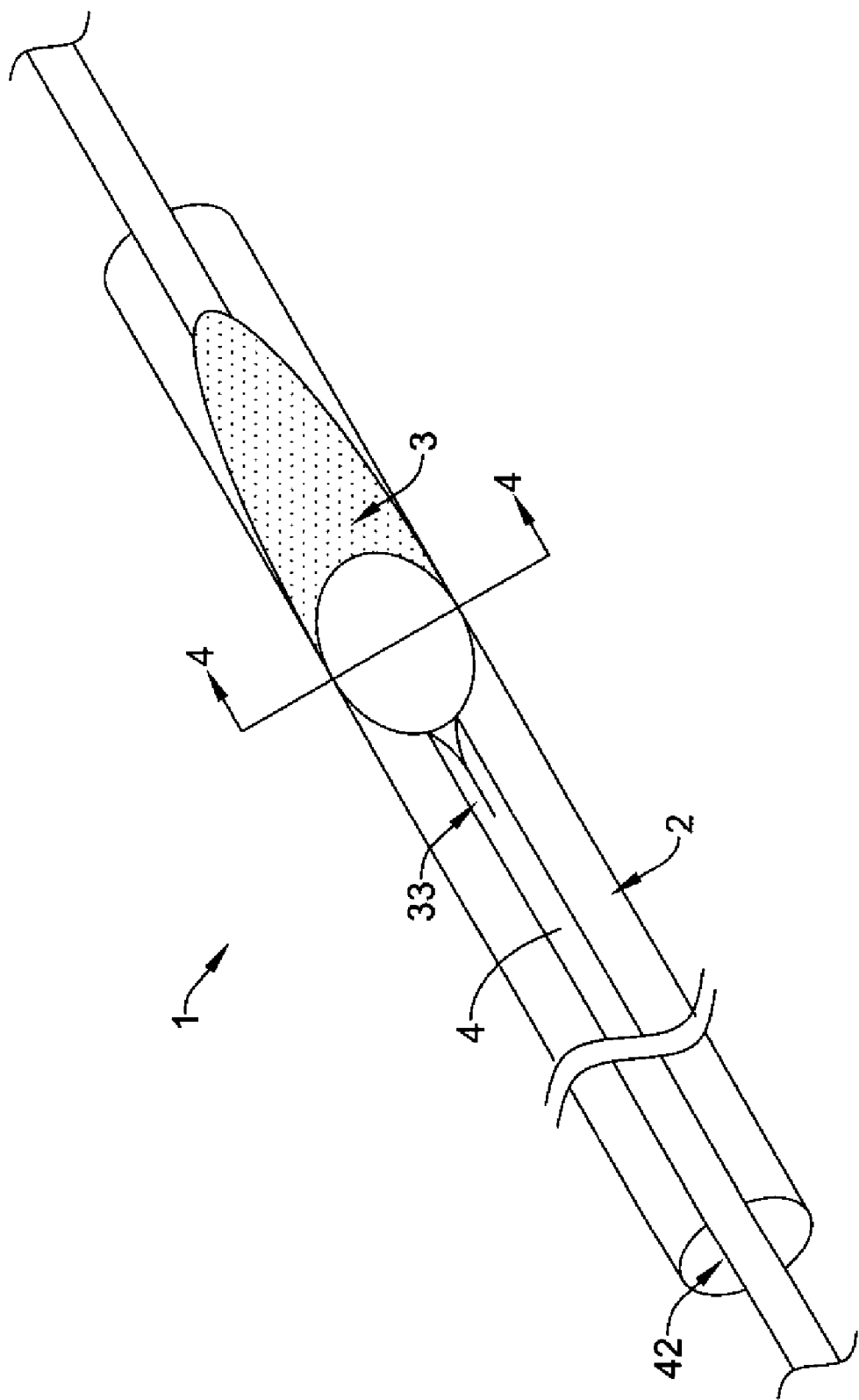
FIG. 3 is a perspective view of the device shown in FIG. 1 with the perfusion and occlusion members in a deployed configuration.

Turning again to FIG. 2, the perfusion member 2 can be formed into the collapsed configuration in any number of ways. For example, an inner surface 24 of the collapsed perfusion member 2 could be adhered to the elongate member outer surface 43 along all or a portion of the inner surface 24. Such adhesion could be by using adhesive, by heating and partially melting one or both of the members, or by other means known to those of skill in the art. The adhesion can be of sufficient strength to maintain the perfusion member 2 around the elongate member 4 as the device 1 is being manipulated within a patient's vasculature. Also, the strength of the adhesion can be sufficiently weak to allow the perfusion member 2 to partially or totally release from the elongate member 4 when the perfusion member 2 is changed from a collapsed to an expanded configuration. This can allow for the perfusion member 2 to be securely in place around the elongate member 4 in a collapsed configuration and, when expanded, it can be released to define an open perfusion lumen 23, as shown in FIGS. 3-5.

In other embodiments, the perfusion member 2 can be predisposed to assuming the collapsed position. In such a case, the perfusion member 2 can be disposed around the elongate member 4, and the predisposition of the perfusion member 2 can cause the perfusion member 2 to wrap around the elongate member 4, for example as shown in FIG. 2. In other cases, all or a portion of the length of the perfusion member 2 can have a bi-stable or limited-stability element 60 disposed in it. For example, this bi-stable or limited-stability element can be predisposed to assuming a first and a second shape. An example of an optional bi-stable or limited-stability element 60 is shown in a first position in FIG. 2 and a second position in FIG. 4. If the bi-stable or limited-stability element 60 has a first and second shape, the first shape can correspond to the collapsed configuration of the perfusion member 2 and the second shape can correspond to the expanded configuration of the perfusion member 2. In some embodiments, the bi-stable or limited-stability element can be predisposed to assume the first shape and, if deformed past a certain point, it can be predisposed to assume the second shape. In other embodiments, the bi-stable or limited-stability element 60 can be predisposed to assume one of an expanded or collapsed configuration.

In addition, other embodiments are also envisioned in which the perfusion member 2 can be disposed about the elongate member 4. For example, turning again to FIG. 2, the folded portions 25 of the perfusion member 2 can be attached in order to dispose the perfusion member 2 around the elongate member 4. If these folded portions 25 are attached, the perfusion member 2 can in some cases essentially form a lumen in which the elongate member 4 can be disposed. The attachment of these folded portions can be by stitching them to one another, by bringing them in close proximity and using an adhesive and/or heat and/or laser welding them to one another, or by other suitable means.

Figure 2B:
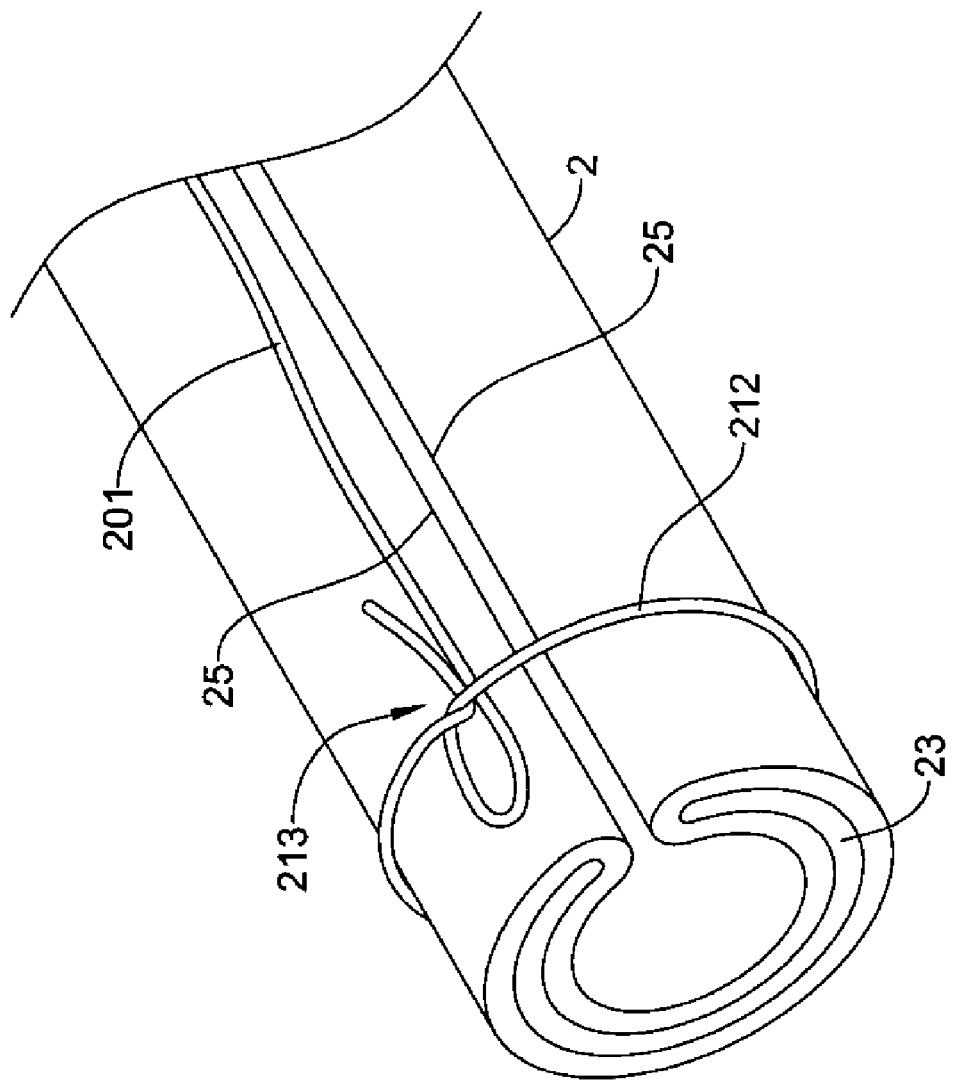

FIGS. 2A and 2B illustrate yet further embodiments of a perfusion member 2 restrained in a collapsed configuration for insertion within the vasculature of a patient. It is noted that the elongate member is not illustrated in FIGS. 2A and 2B for purposes of clarity. Although FIGS. 2A and 2B illustrate gaps defining the lumen 23 of the perfusion member 2 between adjacent folds of the perfusion member 2, it is to be appreciated that the spacing between folds is greatly augmented for illustrative purposes only. The perfusion member 2 is collapsed and folded, defining two longitudinal edges or creases 25. The collapsed perfusion member 2 is rolled into an annular configuration around an elongate member (not shown).

As shown in FIG. 2A, one or a plurality of strands or filaments such as one or more sutures 200 may be used to restrain the longitudinal edges or creases 25 proximate to one another, holding the perfusion member 2 in the collapsed annular configuration. A pull member 201 may be attached to or integral with the suture(s) 200. In some embodiments the suture(s) 200 and the pull member 201 may be monolithic, or the suture(s) 200 may be secured to, adhered to, or otherwise attached to the pull member 201. The pull member 201 may extend substantially the entire length of the perfusion member 2, and thus may be accessible proximal of an incision, exterior of the body of the patient during a medical procedure. The actuation of the pull member 201 proximally may release the suture(s) 200, allowing the perfusion member 2 to expand when desired. In some embodiments, instead of extending exterior of the perfusion member 2, the pull member 201 may extend through the central passage formed by the perfusion member 2 in the collapsed annular configuration.

As shown in FIG. 2B, one or more strands or other filaments 212 may be formed into one or more loops which encircle the perfusion member 2 to hold the perfusion member 2 in the collapsed annular configuration. In some embodiments the strand(s) or filament(s) 212 and the pull member 201 may be monolithic, or the strand(s) or filament(s) 212 may be secured to, adhered to, or otherwise attached to the pull member 201. The one or more strands or other filaments 212 may be selectively released by retraction of the pull member 201 proximally such that the perfusion member 2 is allowed to expand. The strand(s) or filament(s) 212 may be formed into a knot 213, such as a "slip knot" or other type of releasable knot or interlacement, which may securely hold the perfusion member 2 in the collapsed annular configuration until the pull member 201 is retracted proximally. In some embodiments, the free end of the strand(s) or filament(s) 212 may be secured to the perfusion member 2, or in other embodiments, the free end of the strand(s) or filaments) 212 may be loose from the perfusion member 2 such that upon expanding the perfusion member 2 (e.g., releasing or untying the knot 213) the strand(s) or filament(s) 212 and/or the pull member 201 may be removed from the vasculature. In some embodiments, instead of extending exterior of the perfusion member 2, the pull member 201 may extend through the central passage formed by the perfusion member 2 in the collapsed annular configuration. In addition, any of the above methods for forming the perfusion member 2 into a collapsed and/or expanded configuration can be used in combination with one another.

In some cases, when using a bi-stable or limited-stability element, when attaching the folded portions 25 to one another, or when using other suitable methods of disposing the perfusion member 2 about the elongate member 4, the perfusion member 2 and the elongate member 4 can remain unattached to one another. In some cases, the perfusion member 2 and the elongate member 4 can be longitudinally translatable with respect to one another.

Turning to FIG. 3, a perspective view of a device 1 is shown with the perfusion member 2 and the occlusive member 3 both in an expanded configuration. In this figure, the perfusion member 2 and the occlusive member 3 are eccentrically disposed about the elongate member 4. In FIGS. 4 and 5, cross-sections of several possible configurations of eccentrically placed perfusion 2 and occlusive 3 members are shown. In FIGS. 4 and 5, the occlusive member 3 can be any of the occlusive members discussed in this application and the perfusion member 2 can be any of the perfusion members discussed herein.

In FIG. 4, the occlusive member 3 is eccentrically disposed to one side of the elongate member 4, and the perfusion member 2 is eccentrically disposed on the opposite side of the elongate member 4. In addition, the perfusion member 2 and the occlusive member 3 can be placed at other intervals around the surface of the elongate member 4, for example at a 90 degree interval around the elongate member 4 with respect to one another.

In the example shown in FIG. 4, the perfusion member 2 and the occlusive member 3 are shown as they might deploy to their expanded configurations when they are not constrained by a vessel, for example a vessel of a patient. An alternate configuration is shown in FIG. 5, where the perfusion member 2 and the occlusive member 3 can complement one another in order to match a cross-sectional shape of a body lumen. In this example, the perfusion member 2 and the occlusive member 3 complement one another to form a generally round shape, which can substantially match a cross-sectional shape of a blood vessel 70. As also shown in FIG. 5, the perfusion member 2 and the occlusive member 3 can be attached to one another, for example at points 50. This attachment can facilitate the perfusion member 2 and the occlusive member 3 in complementing one another to form a specific shape (for example, the round shape that is shown in FIG. 5), even when the perfusion member 2 and the occlusive member 3 are deployed outside of a body vessel, or when they are deployed in a body vessel that is larger than the deployed size of the perfusion member 2 and the occlusive member 3 together.

As shown in FIG. 5, the occlusive member 3 can substantially occlude a portion of the cross-section of vessel 70. The remainder of the vessel can at the same time accommodate the elongate member 4 and the perfusion member 2, and any other structures that are disposed within the vessel 70. In some examples, the occlusive member 3 can, when in an expanded configuration, occlude 30% or more, 40% or more, 50% or more, or 75% or more of the cross-section of the vessel 70. Alternatively, and as mentioned above, some embodiments can allow for the occlusive member 3 to be advanced independently of the perfusion member 2. In such a case, the occlusive member 3 can be deployed to an expanded configuration and can substantially occlude the entire cross-section of the vessel 70. Also, in some embodiments, the occlusive member 3 can be deployed into an expanded configuration while the perfusion member 2 remains substantially or entirely in a collapsed configuration. In such a case, the occlusive member 3 can occlude a larger fraction of the cross-section of vessel 70, for example 50% or more, 60% or more, 70% or more, 75% or more, 80% or more, 90% or more, or 95% or more of the cross-section of the vessel 70.

Figure 6:
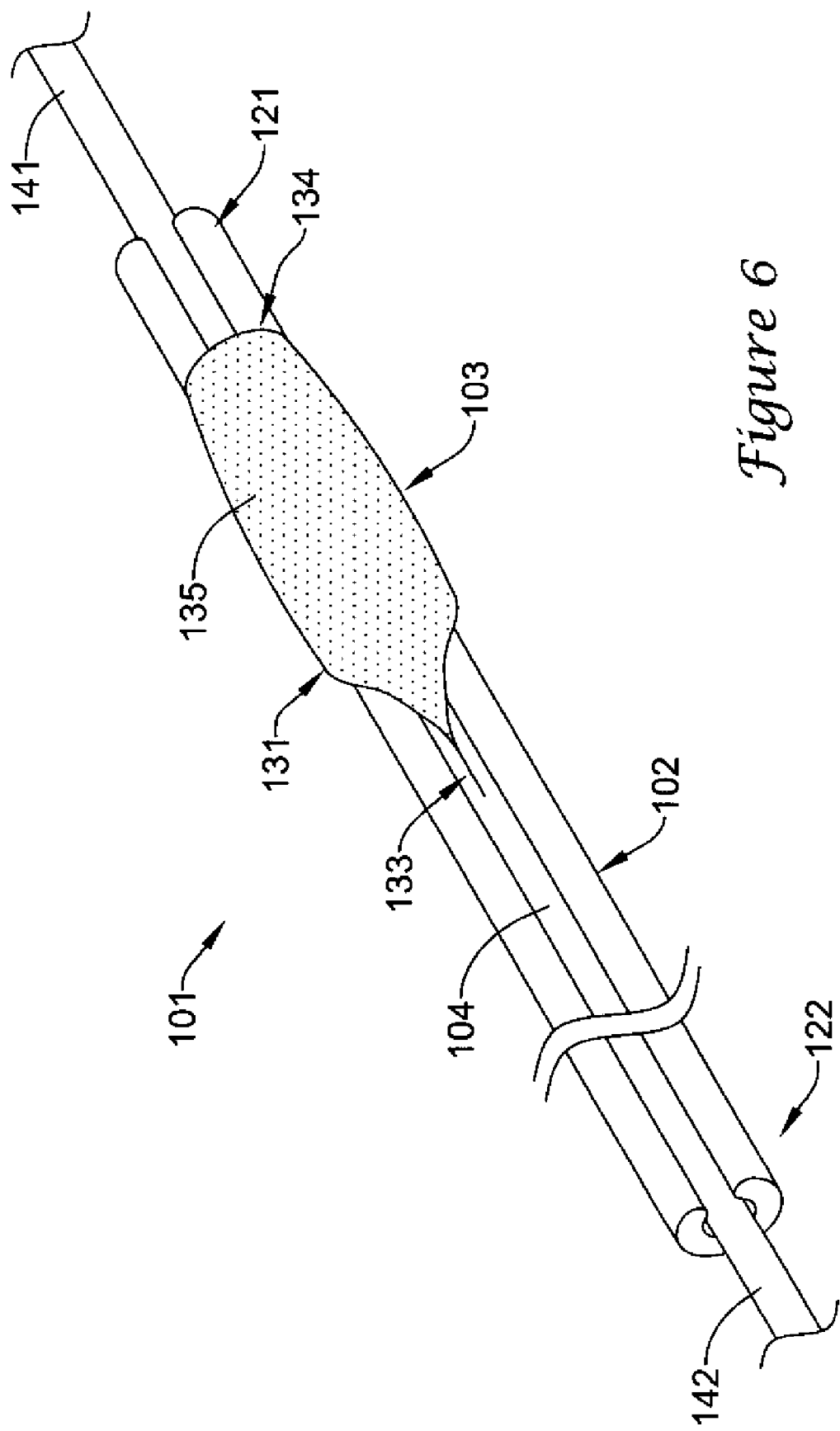
Figure 8:
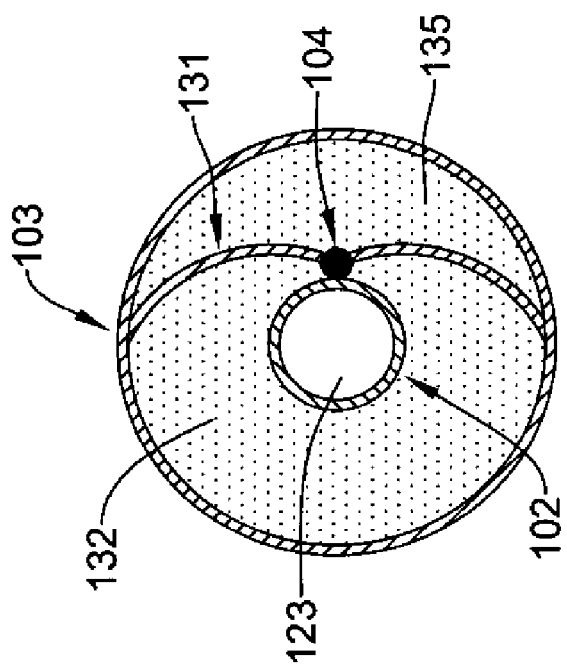
FIG. 8 is a cross-sectional view of a portion of the device shown in FIGS. 6 and 7.

Other configurations are also possible for a combination perfusion and occlusion device. For example, FIGS. 6-8 show an alternate embodiment where a device 101 has an occlusive member 103, an elongate member 104 and a perfusion member 102. The occlusive member 103 is disposed round both the elongate member 104 and the perfusion member 102. The elongate member 104 has a proximal end 142 and a distal end 141 and the perfusion member 102 has a proximal end 122 and a distal end 121. The occlusive member 103 can be any type of occlusive member that is discussed in this application and the perfusion member 102 can be any of the perfusion members discussed herein. As shown in the example of FIGS. 6-8, the occlusive member 103 can be a filter with a support hoop 131 that defines a filter opening 132. The occlusive member 103 can also have a filter material 135, which can be similar to any of the filter materials discussed above with respect to FIG. 1. The filter material 135 can extend from the support hoop 131 to a distal end 134 of the occlusive member 103. At the distal end 134 of the occlusive member 103, the filter material 135 can be attached round the elongate member 104, around the perfusion member 102, or around both. In some cases, a proximal extension 133 can extend from support hoop 131, and this proximal extension 133 can be attached to the elongate member 104 in addition to or instead of attaching the support hoop 131 to the elongate member 104, similar to the arrangement discussed above with respect to FIG. 1.

Further, FIG. 7 shows the device 101 of FIG. 6, where both the perfusion member 102 and the occlusive member 103 are in their expanded configurations. FIG. 8 further shows a cross-sectional view of the embodiment of FIG. 7. In this cross-sectional view, the perfusion member 102, which can define perfusion lumen 123, is shown concentrically disposed, and the elongate member 104 eccentrically disposed, within the occlusive member 103. Other configurations are also contemplated. For example, the perfusion member 102 could be eccentrically disposed and the elongate member 104 could be concentrically disposed within the occlusive member 103. In addition, both the perfusion member 102 and the elongate member 104 could be eccentrically disposed within the occlusive member 103.

In addition, other configurations are contemplated for the collapsed configurations of the perfusion 102 and occlusive members 103. In the collapsed configuration, the perfusion member 102 can be disposed along or around the elongate member, for example in any manner described herein. Further, when the occlusive member is in its collapsed configuration, the occlusive member can be disposed along or around the elongate member, the perfusion member, or both.

Figure 9:
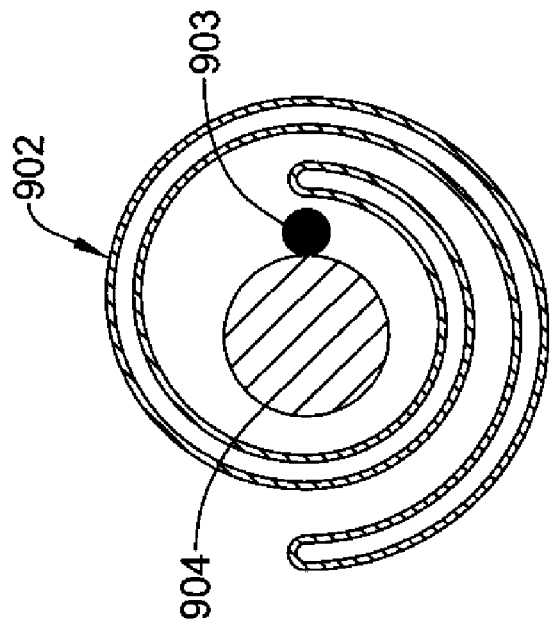
FIG. 9 is a cross-sectional view of an alternative embodiment of a combination occlusion and perfusion device.

Turning now to FIG. 9, a cross-sectional view of an alternative embodiment is shown. In this example, a perfusion member 902 is disposed around both an elongate member 904 and an occlusive member 903. The perfusion member 902, when in a collapsed configuration, can be wrapped around the occlusive member 903 and the elongate member 904 less than one revolution (as shown in FIG. 2), one revolution, at least one revolution or more than one revolution. In FIG. 9, the perfusion member 902 is shown wrapped around the elongate member 904 and the occlusive member 903 a total of approximately 540 degrees. The perfusion member 902 can also be wrapped around the elongate member 904 and the occlusive member 903 a total of more or less than 540 degrees, for example 450, 630 or 720 degrees, or more.

In some cases, objects in a body lumen may interfere with the deployment of a perfusion member. For example, if there is an occlusion in a vessel, a collapsed perfusion member can be advanced around the occlusion, but the occlusion may partially or completely prevent the perfusion member from assuming an expanded configuration. Further, if an occlusive member causes elevated pressure on one side of the occlusive member, the perfusion member may be partially or completely prevented from assuming an expanded configuration in the presence of this elevated pressure. This elevated pressure could be the result of using an occlusive member that partially or totally restricts the flow of fluids through a body lumen past the occlusive member. For example, a balloon occlusive member or a filter that becomes plugged with emboli may cause elevated pressure on an upstream side of the occlusive member. In such cases, it may be desirable to have structure which allows the perfusion member to open a perfusion lumen, even in the presence of occlusions or elevated pressure or other impediments.

Figure 10:
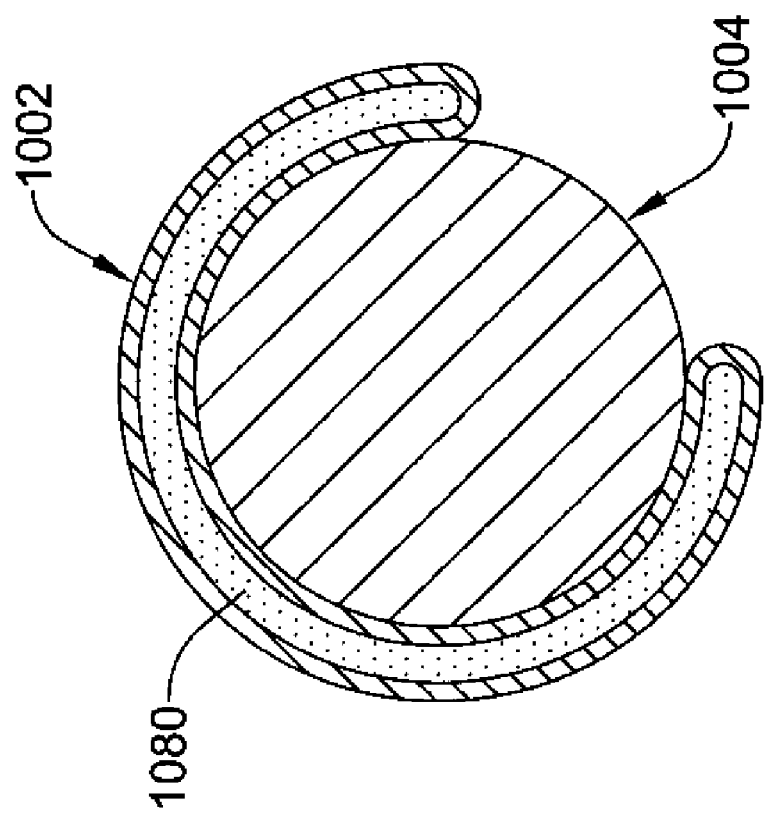
FIG. 10 is a cross-sectional view of a distal portion of an alternative embodiment of a combination occlusion and perfusion device.

Turning to FIG. 10, a perfusion lumen 1002 is shown disposed around an elongate member 1004. This cross-sectional view can be taken at a distal portion of the combination perfusion and occlusion device, for example at the distal end of the device. A seal 1080 can be formed that partially or entirely seals the end of the perfusion member 1002. The seal 1080 can be, for example, an adhesive or weld that adheres the inner wall 1024 to itself when the perfusion member 1002 is in a collapsed configuration, as shown in FIG. 10. This seal can be sufficiently strong such that pressure is allowed to build up in the perfusion member 1002. This pressure can help open a lumen through the perfusion member 1002, even in the presence of elevated pressure or occlusions or other impediments to the perfusion member assuming an expanded configuration. Further, when a certain pressure is reached, the seal 1080 can be partially or entirely broken or opened and the perfusion member can be used to perfuse fluids.

Figure 11B:
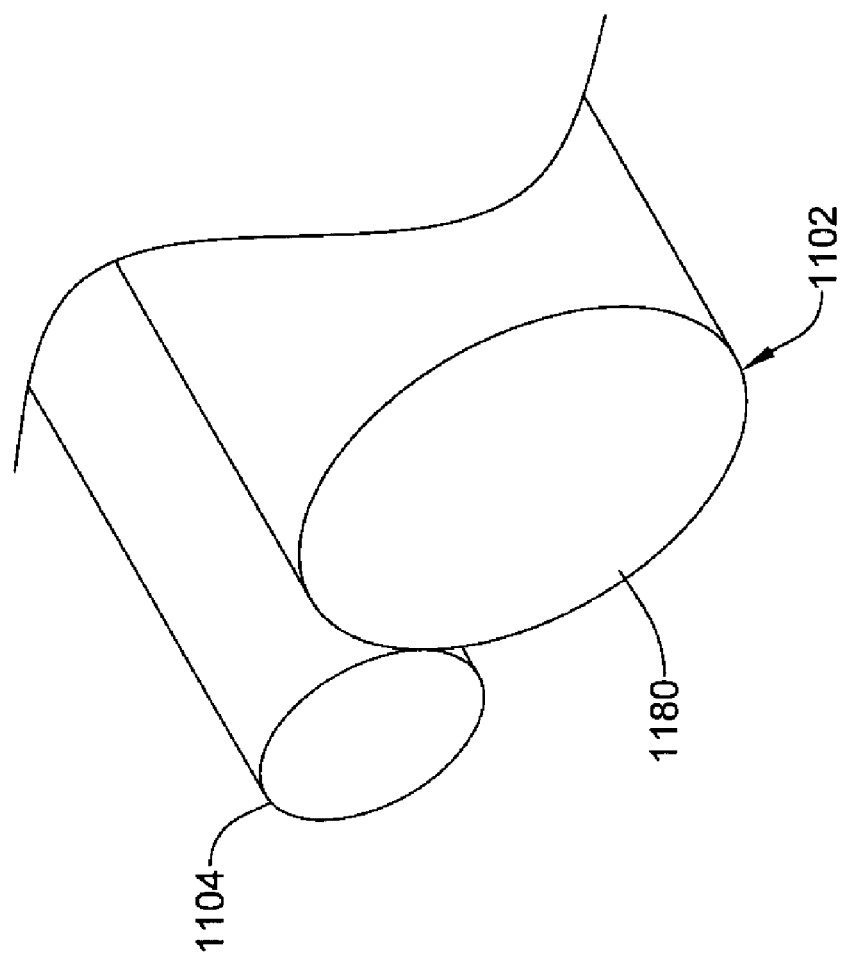
FIGS. 11A and 11B show, respectively, a collapsed and expanded perfusion member with a seal in a distal portion of the perfusion member.
Figure 11A:
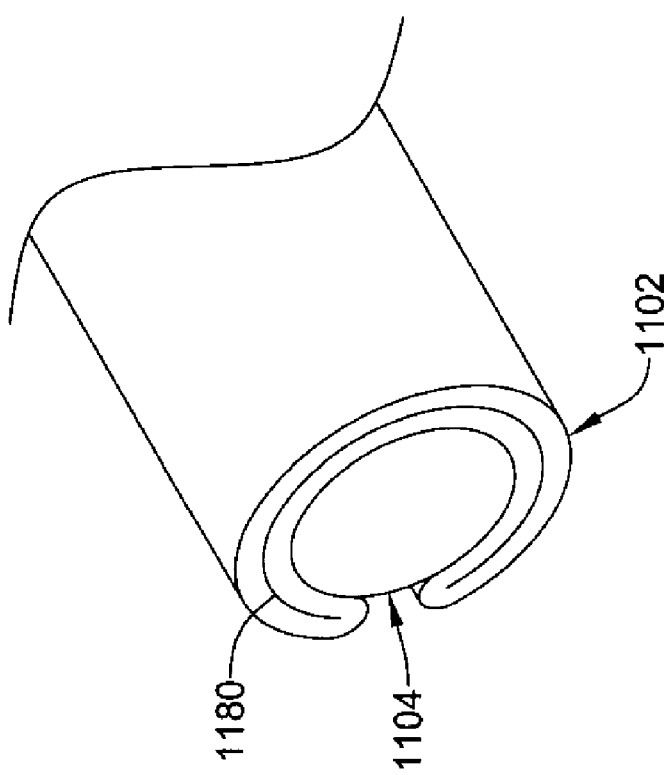

Turning to FIGS. 11A-11B, the seal 1180 can be a flap that can be disposed within the perfusion member 1102. FIG. 11A shows the flap 1180 in a perfusion member 1102 that is in a collapsed configuration and FIG. 11B shows the flap 1180 in perfusion member 1102 when the perfusion member 1102 is in an expanded configuration. The perfusion member 1102 can be disposed along an elongate member 1104 as described in any of the embodiments of this application. The flap 1180 can be in a distal portion of the perfusion member 1102, for example at the distal end, and the flap 1180 can partially or entirely seal the perfusion member 1102. The flap 1180 can cause a build-up of pressure within the perfusion member 1102, which, as mentioned above, can help open a perfusion lumen along the length of the perfusion member 1102. Once a certain pressure has been reached, the flap 1180 can open, allowing fluids to be perfused through the perfusion member 1102.

Other structures are also contemplated that can partially or entirely seal the perfusion member. For example, the perfusion member could have a distal portion or a distal end that is strongly predisposed to maintaining a collapsed or partially collapsed configuration. In some embodiments, this strong predisposition could be caused by a support member that is predisposed to assume the collapsed configuration. In such a case, the distal portion or end could partially or entirely restrict the flow of fluids, allowing pressure to build up in the perfusion member.

In addition, any of the above sealing structures that can partially or entirely restrict the flow of fluids through the perfusion member can be used to maintain a level of back pressure. After a perfusion member has been opened (whether of not there were obstructions, elevated pressures, or other impediments blocking its opening in the first place), the sealing structures can continue to at least partially restrict fluid flow, allowing a certain level of back pressure to build up within the perfusion member. Maintaining a certain level of back pressure can be useful, for example in cases where the perfusion member comprises an elastic material. In any case, the back pressure can ensure that the perfusion member assumes and maintains an expanded configuration against a vessel wall or other structures.

Figure 12:
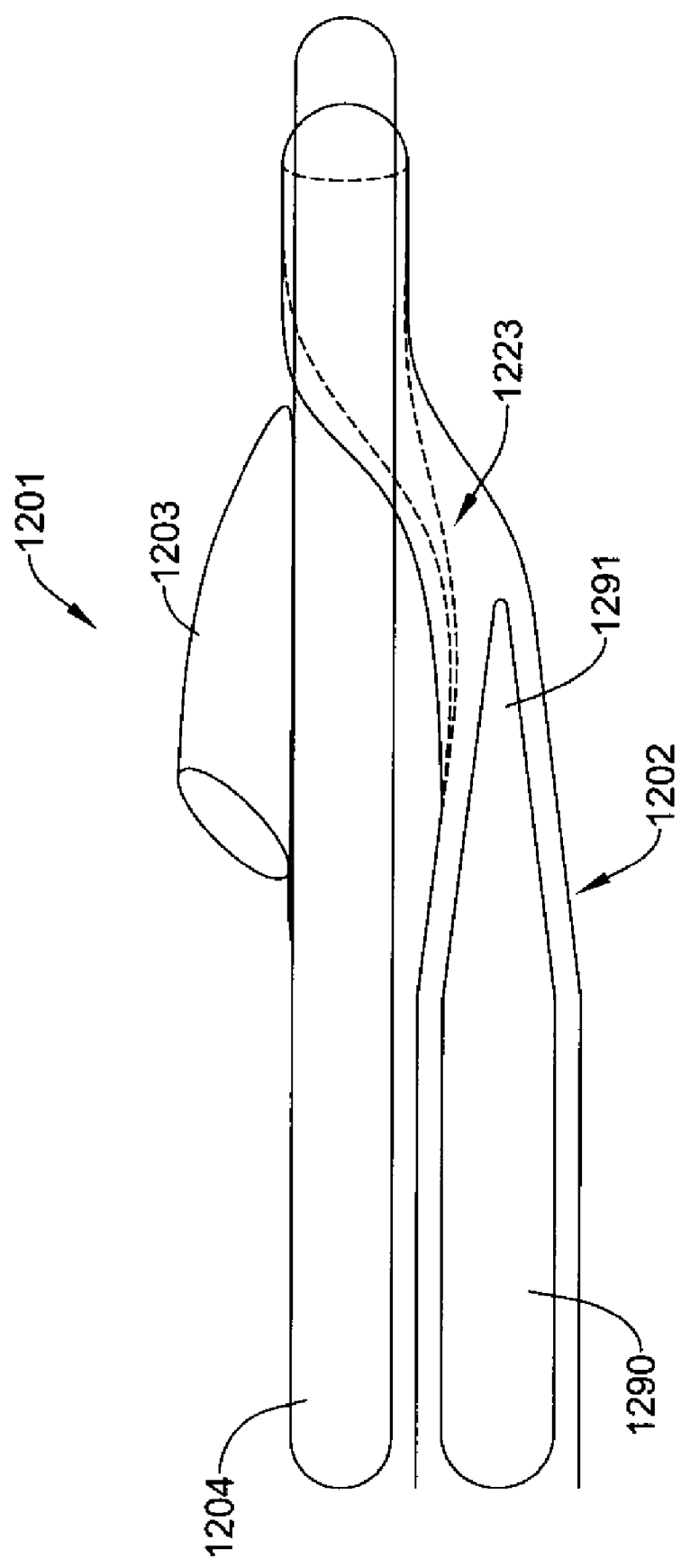
FIG. 12 is a longitudinal cross-section of an embodiment of a combination occlusion and perfusion device which can also include a dilation catheter.

Turning now to FIG. 12, alternate structures and methods are shown for deploying a perfusion member 1202. The structure can comprise a perfusion member 1202, an elongate member 1204, an occlusive member 1203 and a dilation member 1290. The perfusion 1202, elongate 1204 and occlusive 1203 members can be similar to any of the structures described herein. Further, a dilation member 1290, for example a dilation wire or catheter, can be included in the combination occlusion and perfusion device 1201. In some cases, a distal portion 1291 of the dilation member 1290 can be tapered. The dilation member 1290 can be shaped and configured such that it can fit within the is perfusion member 1202 when the perfusion member 1202 is in an expanded configuration. The distal portion 1291 of the dilation member 1290 can, for example, be placed within the perfusion member lumen 1223 at a proximal end of the perfusion member.

The dilation member 1290 can then be advanced through the perfusion member 1290. In examples where the perfusion member 1202 is disposed around the elongate member 1204 (as shown in FIG. 12), advancing the dilation member 1290 can cause the perfusion member 1202 to be removed from the elongate member 1204. In any case, advancing the dilation member 1290 can cause the perfusion member 1202 to expand toward its expanded configuration. The advancement of the dilation member 1290 can also assist in providing an open lumen through the perfusion member 1202, for example in cases where excessive pressure, occlusions or other impediments are preventing the perfusion member 1202 from being able to assume a fully expanded configuration. The perfusion member, when in its collapsed configuration, has a first longitudinal portion that is disposed around a portion of the elongate shaft and a second longitudinal portion that is disposed along side the elongate shaft, where the first portion is distal of the second portion (as shown in FIG. 12).

As an additional example, the bi-stable or limited-stability elements that are discussed above can also assist the perfusion member in assuming an expanded configuration in cases where excessive pressure, vessel occlusions or other impediments are preventing the perfusion member from being able to expand entirely to its expanded configuration.

The combined perfusion and occlusion device can also have other alternative configurations. For example, the elongate member can be disposed inside the perfusion member. In such a case, the occlusion member can be disposed about or on the perfusion member. With the elongate member disposed inside the perfusion member, the perfusion member can be attached to the elongate member or, in some cases, the elongate member and the perfusion member can be longitudinally translatable with respect to one another. The configuration of the perfusion member, the occlusive member and the elongate member with respect to one another can generally be altered depending on the application.

In addition, the combination perfusion and occlusion device can comprise or be used in combination with other types of interventional devices. For example, the angioplasty devices, atherectomy devices, or other interventional devices can be passed over all or a portion of the combination perfusion and occlusion device. For example, once the combined perfusion and occlusion device is in place, an interventional device with a lumen can be passed over the combined perfusion and occlusion device. In some cases, the lumen of the interventional device can be sufficiently large to allow the combination perfusion and occlusion device to be disposed in the lumen, and in some cases the lumen can be sufficiently sized to accommodate a perfusion member of the combined perfusion and occlusion device when the perfusion member is partially or entirely in an expanded configuration. In other cases, an interventional device can be introduced to a body vessel along side the combination perfusion and occlusion device, or through a lumen in the elongate member of the combination perfusion and occlusion device.

Other additional features can also be included in any of the above described combination perfusion and occlusion devices. For example, one or more pressure sensors could be placed along the combination occlusion and perfusion device. In one embodiment, pressure sensors can be placed proximal and distal of any occlusive members. Pressure readings can be taken in order to monitor either the nominal pressure or the pressure difference between two points, or both. In one example, if a filter is acting as the occlusive member, the pressure difference between a point proximal and a point distal of the filter can be taken. Higher pressure difference between these points can indicate that the filter is becoming plugged and sufficient blood or fluid flow may not be passing through the filter. In such a case, a perfusion member, if not already present, can be advanced through the patient's vasculature, for example any of the perfusion members discussed herein. Perfusion (or increased perfusion) can be started in order to prevent possible ischemia.

In addition, it is contemplated that portions of the combined perfusion and occlusion device can comprise radiopaque portions and/or radiopaque structures such as marker bands can be added to the device. Radiopaque portions of the device can be formed by incorporating radiopaque members into the construction of the device. Such radiopaque members can be, for example, radiopaque metals or polymers or composite materials with radiopaque materials dispersed within the polymer or composite. For example, one or more radiopaque portions or marker bands could be disposed at, in, or around an occlusive member so that a physician can monitor the position of the occlusive member. Other portions could similarly be made radiopaque, for example a distal portion or distal end of an occlusive member, a support structure of an occlusive member, or a distal portion or distal end of a perfusion member, or any combination thereof. All of, or portions of, the combination perfusion and occlusion device can also be made compatible and/or visible with MRI.

The materials of construction of the combined perfusion and occlusion device can vary depending on the desired properties of the device. The elongate member can be a metal or a polymer. As an example, the elongate member could be linear elastic or superelastic Nitinol, stainless steel, or other metals or metal alloys. In addition, the elongate member could comprise a polymer. The elongate member can have a variable flexibility along its length, for example it could be more flexible in a distal region compared to a proximal region. In some embodiments, such a change in flexibility could result from a variation in the cross-sectional area of the elongate member along its length. A variation in flexibility could also result from a change in the material composition along the length of the elongate member; for example, the elongate member can comprise a single elongate member that varies in composition along its length and/or it can comprise multiple elongate members that differ in composition or in other properties such as cross-sectional area. Further, the elongate member can have a round cross-sectional shape, as shown in the Figures. The elongate member could also have other cross-sectional shapes; for example, the cross-sectional shape could be square, triangular, rectangular, oval, polygonal, or other shapes, or the cross-sectional shape could vary along the length of the elongate member.

In yet another embodiment, a method of occluding a body vessel is disclosed. In one step, a combination perfusion and occlusion device can be provided. For example, any of the combination perfusion and occlusion devices described in this application can be provided. A perfusion member can be inserted into the vasculature of a patient and its distal end can be advanced to a point proximate a treatment area, for example a point proximal or distal a treatment area. An occlusive member can be inserted into the vasculature of a patient and advanced to a point proximate a treatment area, for example a point distal or proximal of the treatment area. An elongate member can be inserted into the vasculature of a patient and its distal end can be advanced to a point proximate a treatment area, for example a point proximal or distal the treatment area. In addition, any combination of the perfusion member, elongate member and occlusive member can be inserted simultaneously, or one or more of the members can be inserted and the other members subsequently inserted, for example in the methods described earlier in this application.

As one example, the perfusion member could be advanced over the elongate member, as discussed earlier.

Further, the method can include the step of deploying the perfusion member from a collapsed configuration to an expanded configuration. The method can also include the step of deploying the occlusive member from a collapsed configuration to an expanded configuration. The perfusion member can be deployed before the occlusive member, or vice versa. In addition, both the perfusion member and the occlusive member can be deployed simultaneously, or only one of these two members can be deployed. The method can also include the step of perfusing fluids through the perfusion member. The perfusion member and the occlusive member can be deployed in any of the ways that are discussed in this application.

In other embodiments, the perfusion member can have a seal, for example any of the seals described herein. As mentioned above, the seal can have a predetermined pressure above which it will open. The method can include the step of introducing fluids to the perfusion member up to the predetermined pressure, and subsequently exceeding that pressure in order to partially or entirely break or open the seal.

Further, any of the above methods can also include the step of providing a dilation member, such as any of the dilation members that are described with respect to FIG. 12. The method can further include the step of opening or deploying the perfusion member by inserting the dilation member through all or a portion of the perfusion member.

Any of the above methods could also include the step of inserting another interventional device into the patient's vasculature, for example along the elongate member, along the perfusion member, along both the elongate and perfusion members, or through a lumen in the elongate member or the perfusion member. Such interventional devices could be, for example, an embolus extractor, a distal protection device, a balloon catheter, a stent placement catheter, an embolic coil placement device, or the like.

Figure 13A:
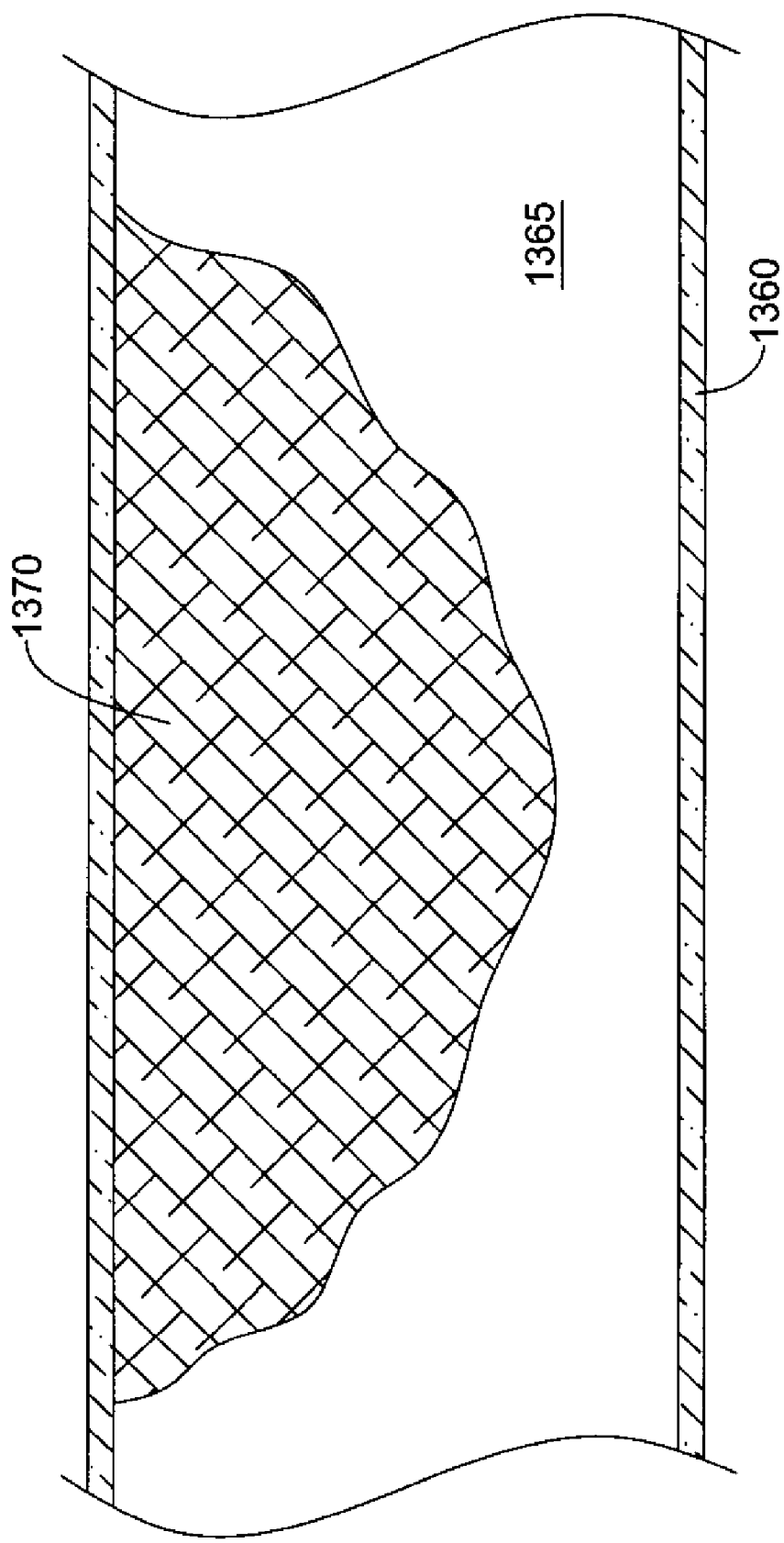
FIGS. 13A-13F show an alternative method and structure for introducing a perfusion or combination perfusion and occlusion device into the vasculature of a patient.

In some cases, the combination occlusion and perfusion device must be passed around an obstruction in a patient's vasculature. An exemplary method of passing an obstruction is shown in FIGS. 13A-13F. FIG. 13A illustrates an occlusion 1370, which may be, for example, a thrombus or thromboembolus, obstructing the lumen 1365 of a vessel 1360. The occlusion 1370 may partially or entirely inhibit the flow of blood through the vessel 1360, causing medical complications to the patient.

Figure 13B:
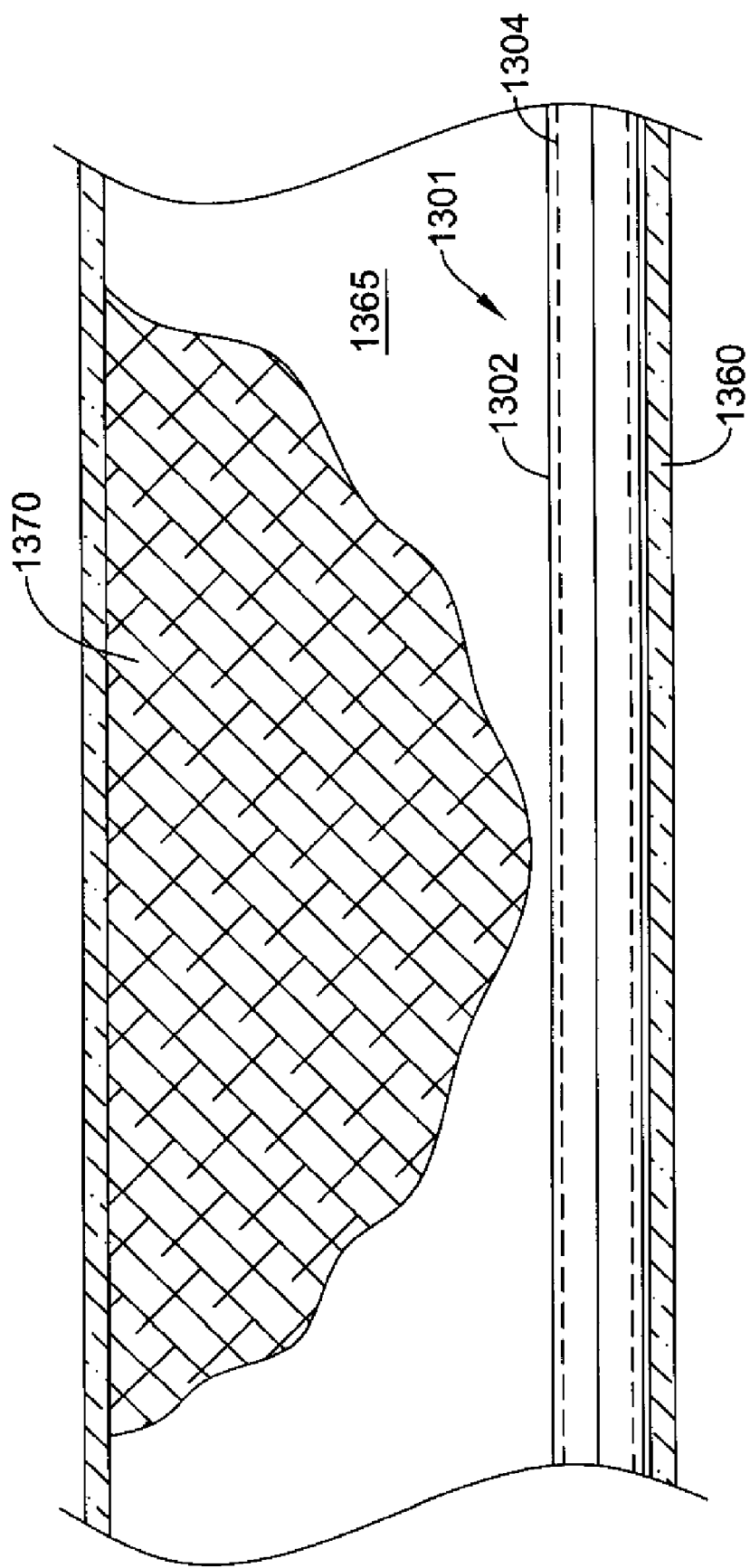

During a medical procedure (e.g., any of the procedures and methods described herein), a combination perfusion and occlusion device 1301 (which can be any of the combination perfusion and occlusion devices described herein), having the perfusion member 1302 tightly folded and wrapped around the circumference of the elongate member 1304, may be advanced through the vasculature through the vessel 1360 to a location proximate the occlusion 1370, as shown in FIG. 13B. (Note that in FIG. 13B the elongate member 1304 is not shown, but is shown in phantom in later figures. Also note that in FIGS. 13B-13F the distal end of the elongate member 1304, and any occlusive member that may be disposed thereon, is to the right of these figures and is not shown. However, the elongate member 1304 can have disposed thereon any of the occlusive members described herein.) The perfusion member 1302 may be releasably secured to the elongate member 1304 such that longitudinal movement of the elongate member 1304 corresponds to equivalent longitudinal movement of the perfusion member 1302. The perfusion member 1302 may also be slidable relative to the elongate member 1304. The low profile of the combination device 1301 in the collapsed configuration allows the combination device 1301 to be advanced distal of the occlusion 1370 without dislodging or otherwise adversely disturbing the occlusion 1370.

Figure 13C:
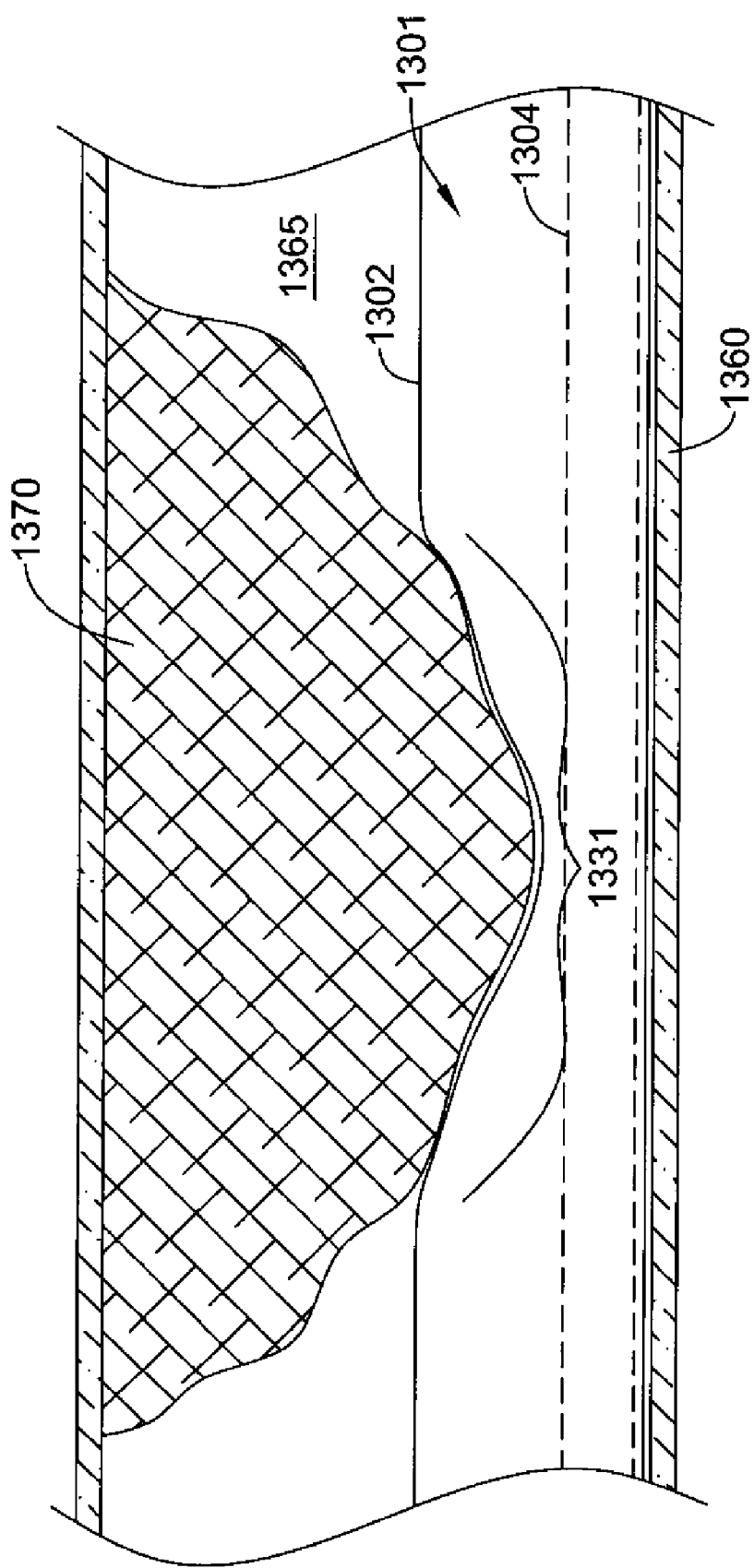

Once positioned across the occlusion 1370, the perfusion member 1302 may be expanded to a larger diameter, as shown in FIG. 13C. For example, fluid pressure may be administered through the lumen 1336 of the perfusion member 1302 from a pressure device coupled to a connector at a proximal end of the perfusion member 1302 proximal of an incision and external of the body of the patient. As shown in the FIGS., the perfusion member 1302 may be expanded to 2 times or more, 2.5 times or more, or 3 times or more of its initial collapsed diameter. In other embodiments, the perfusion member 1302 may be expanded by other means as described herein. For example, a bi-stable member or a dilator may be used to expand the perfusion member 1302, or an outer sheath or suture, restraining the perfusion member 1302 in the collapsed configuration, may be removed, thereby releasing the perfusion member 1302 to be expanded. One of skill in the art, incited by the present disclosure, would understand additional equivalent means of expanding the perfusion member 1302 once properly positioned across the occlusion 1370.

In some embodiments, such as that shown, when expanded, the occlusion 1370 may restrict full expansion of the perfusion member 1302 along a portion of the perfusion member 1302. The constricted portion 1331 of the perfusion member 1302 may conform to the contour of the occlusion 1370 within the vessel 1360. However, in other embodiments the perfusion member 1302 may more fully expand through the region of the occlusion 1370, thus radially compressing the occlusion 1370 against the wall of the vessel 1360.

Once positioned and expanded, the perfusion member 1302 may be used to perfuse a perfusate, such as oxygenated blood or a medicinal fluid, to a location distal of the occlusion 1370. The perfusion member 1302 can also extend further distally past an occlusive member (not shown), delivering the perfusate distally of both the occlusion 1370 and the occlusive member. The perfusate may be administered through the lumen 1336 of the perfusion member 1302 from a pressure device coupled to a connector at the proximal end of the perfusion member 1302 proximal of an incision and external of the body of the patient. Therefore, the perfusion member 1302 may provide perfusate to tissue distal of the occlusion 1370, and in some cases distal of the occlusive member. Even in embodiments in which the perfusion member 1302 retains a restriction attributable to the constricted portion 1331 conforming to the contour of the occlusion 1370, the perfusion member 1302 may allow a sufficient quantity of perfusate to reach tissue distal of the occlusion 1370.

Once expanded, the perfusion member 1302, if releasably connected to the elongate member 1304, may be released from the elongate member 1304 such that the elongate member 1304 may be translated independent of the perfusion member 1302. In the illustrated embodiment, the elongate member 1304 is positioned within the lumen 1336 of the perfusion member 1302. However, as described herein, in other embodiments, the elongate member 1304, once released from the perfusion member 1302 may be positioned generally parallel to and alongside the exterior of the perfusion member 1302. In embodiments wherein the elongate member 1304 is positioned within the lumen 1336 of the perfusion member 1302, the elongate member 1304 may be withdrawn from the lumen 1336 or retained in the lumen 1336 during perfusion of a perfustate through the lumen 1336, as desired.

Figure 13D:
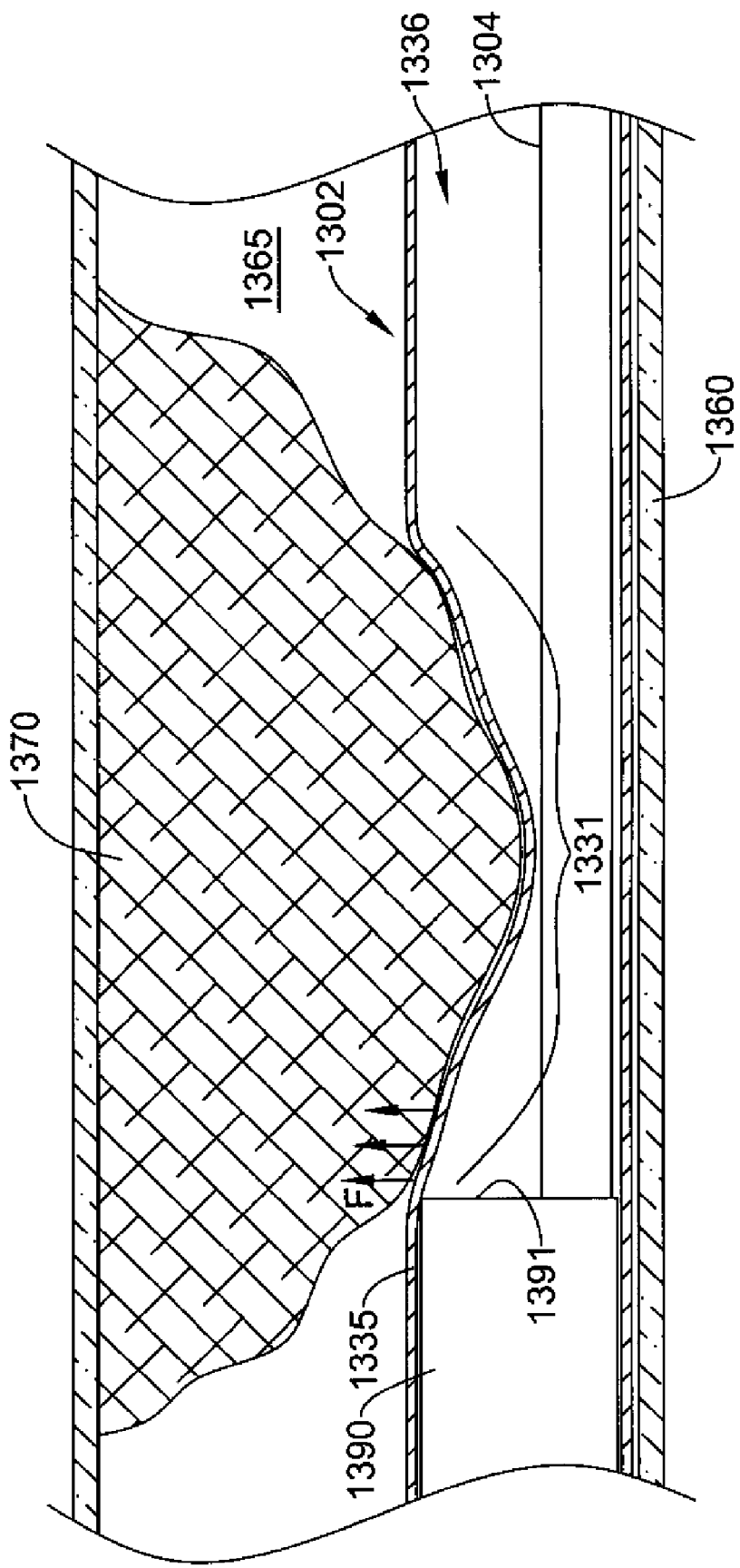

As shown in FIG. 13D, once the perfusion member 1302 has been expanded and released from the elongate member 1304, the elongate member 1304 may be used to track additional medical devices, such as an embolus extractor, a distal protection device, a balloon catheter, a stent placement catheter, an embolic coil placement device, or the like, through the vasculature to a location proximate the occlusion 1370. As shown in FIG. 13D, medical device 1390, illustrated as a catheter, may be advanced over the elongate member 1304 through the lumen 1336 of the perfusion member 1302. A medical device 1390 could also be advanced through the lumen 1336 of the perfusion member 1302 without the elongate member 1304 present (e.g., when an elongate member is positioned outside of the perfusion lumen 1336). Further, it is noted that the elongate member 1304 shown in FIG. 13D could also be in addition to an elongate member disposed outside of the perfusion lumen 1336 shown in FIG. 13D (e.g., any of the embodiments described herein that incorporate an elongate member 1304 along side a perfusion member 1302).

As the medical device 1390 approaches the occlusion 1370, the perfusion member 1302 may act as a "shoehorn" for the medical device 1390. That is, the perfusion member 1302 may facilitate passage of the medical device 1390 distally past the occlusion 1370 without adversely affecting the occlusion 1370 (e.g., dislodging and/or subjecting the occlusion 1370 to shear stresses). As the medical device 1390 approaches the constricted portion 1331 of the perfusion member 1302, resultant of the perfusion member's conformity around the occlusion 1370, the leading edge 1391 of the medical device 1390 may engage the wall 1335 of the perfusion member 1302. As the medical device 1390 is urged further distally, the leading edge 1391 of the medical device 1390 urges the wall 1335 radially outward, subjecting radially compressive forces F upon the occlusion 1370. Unlike circumstances in which the perfusion member 1302 is not initially positioned across the occlusion 1370 prior to advancing a medical device 1390 distal of the occlusion 1370, the occlusion 1370 experiences minimal axial or shear stresses as the medical device 1390 is advanced past the occlusion 1370. This is realized in that the axial displacement of the medical device 1390 is translated into radial forces to the occlusion 1370 by the "shoehorn" effect of the perfusion member 1302. In circumstances in which the medical device 1390 is advanced past the occlusion 1370 without the aid of perfusion member 1302, the longitudinal movement of the medical device 1390 may dislodge the occlusion 1370, pushing it further distally in the vessel 1360, or subject the occlusion 1370 to undesirable levels of shear stresses which could otherwise break off portions of the occlusion 1370 to potentially travel downstream and cause embolic distal vessel occlusion.

Figure 13E:
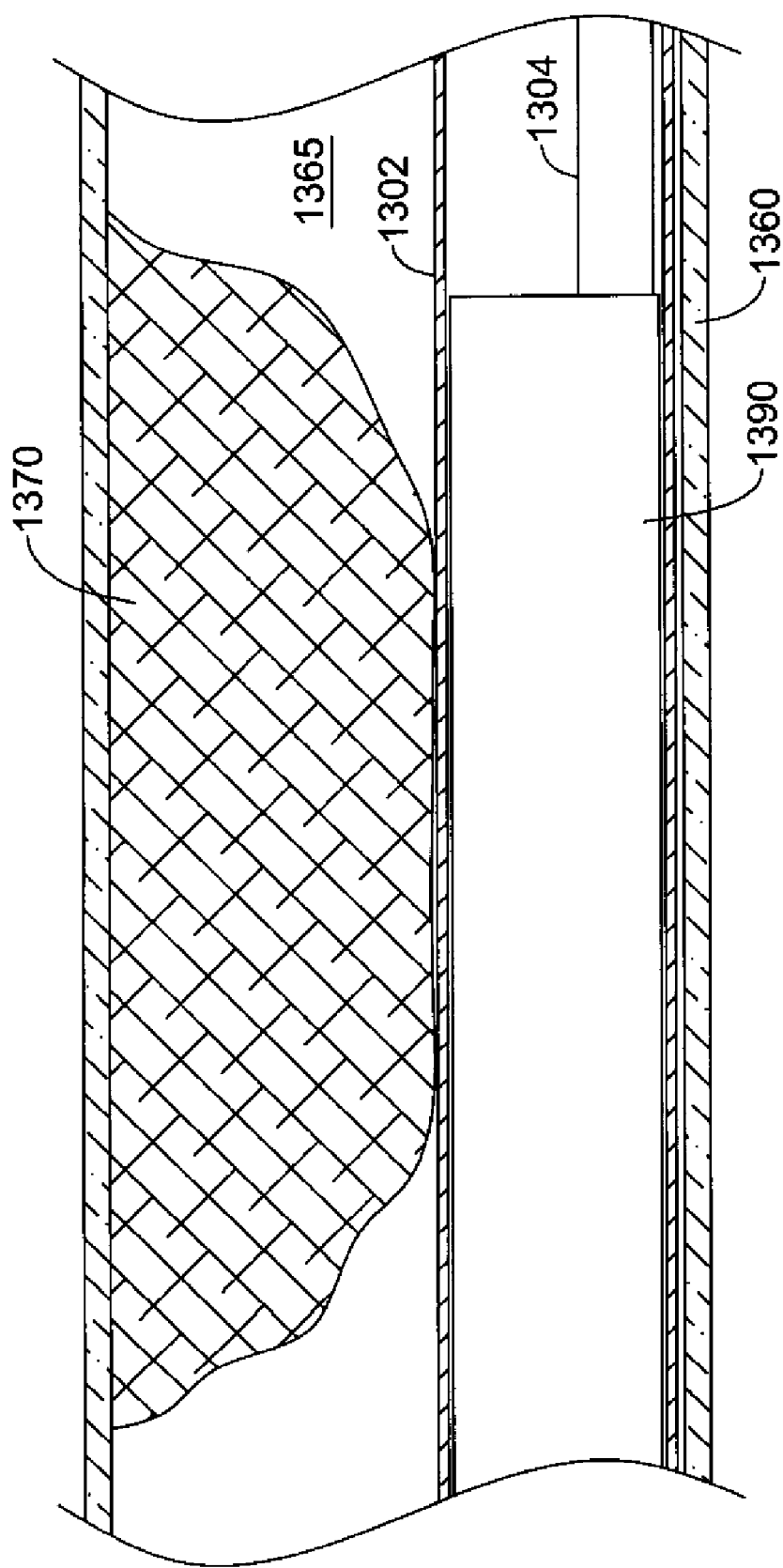
Figure 13F:
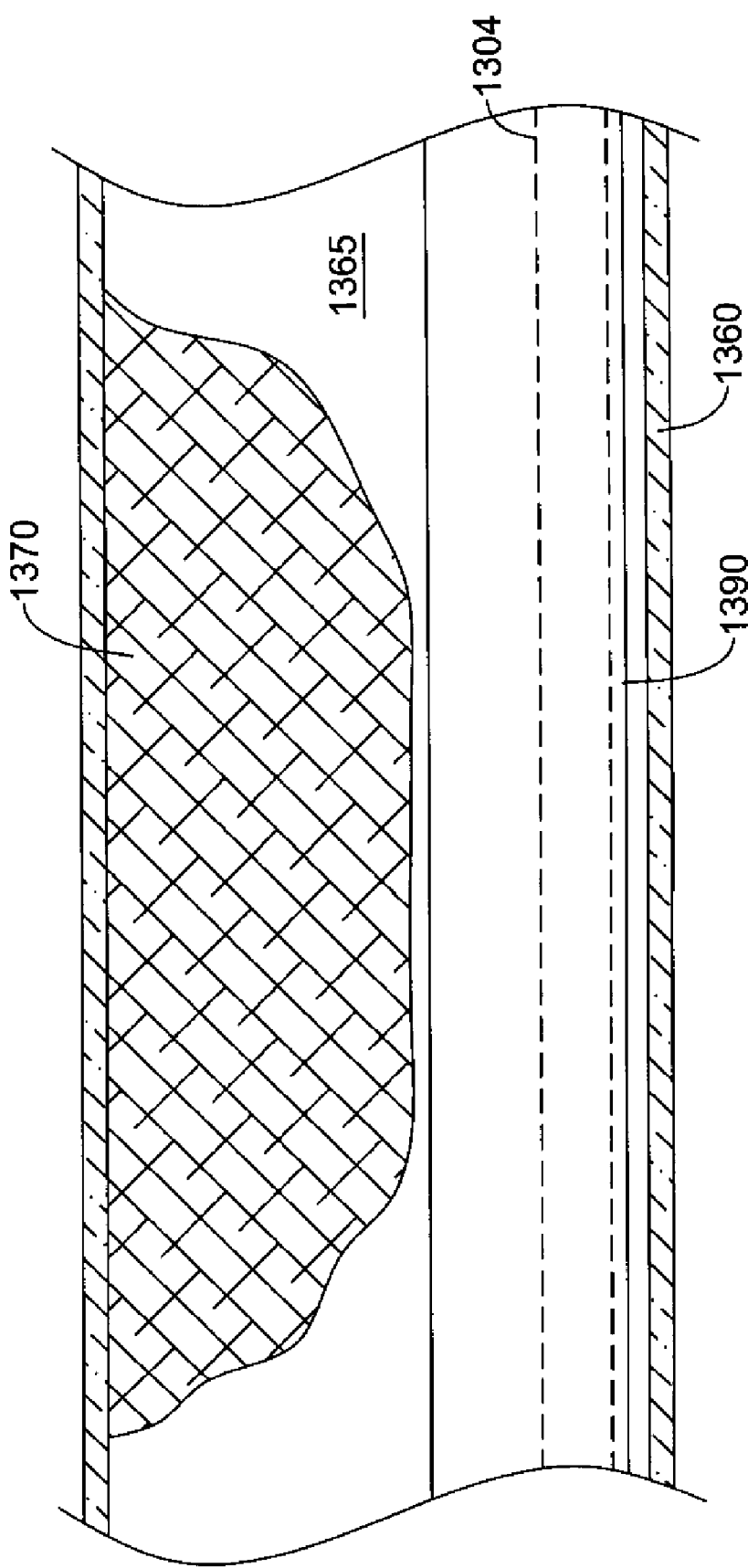

FIG. 13E illustrates the medical device 1390 extending through the perfusion member 1302 to a location distal of the occlusion 1370. The occlusion 1370 is shown radially compressed toward the wall of the vessel 1360, yielding to the enlargement of the perfusion member 1302 as the medical device 1390 is passed therethrough. With the medical device 1390 positioned distal of the occlusion 1370, a further medical procedure may be performed in order to provide treatment, remove the occlusion 1370, or the like. In some instances, once the medical device 1390 has been positioned across the occlusion 1370, the perfusion member 1302 may be withdrawn from the vessel 1360, as shown in FIG. 13F, providing accessibility to the occlusion 1370 to perform a medical treatment.

Figure 14:
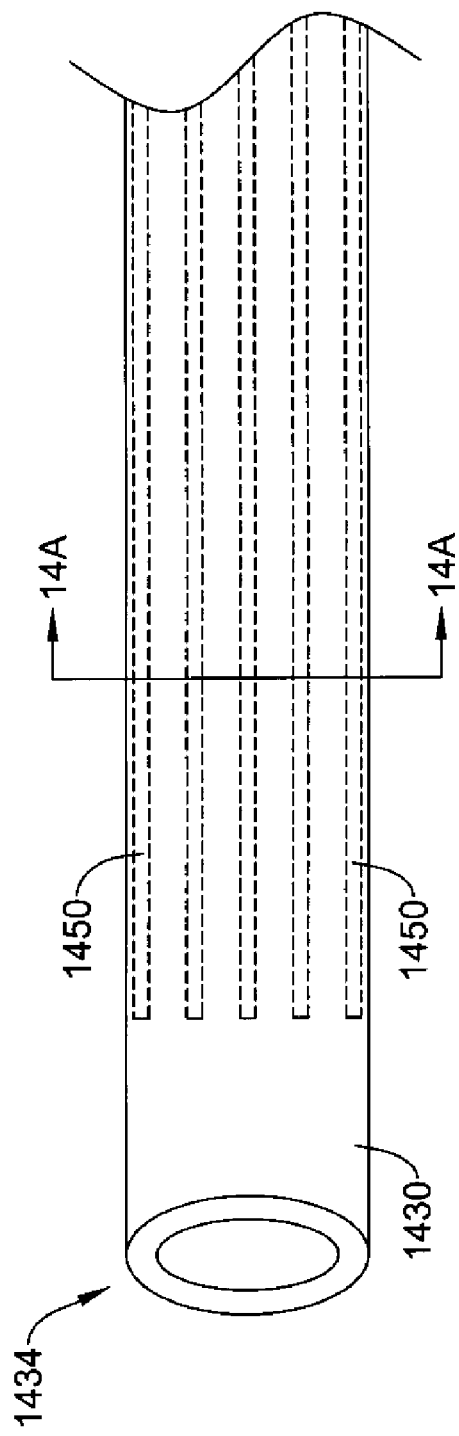
FIGS. 14 and 14A show an alternative structure for a perfusion member.
Figure 14A:
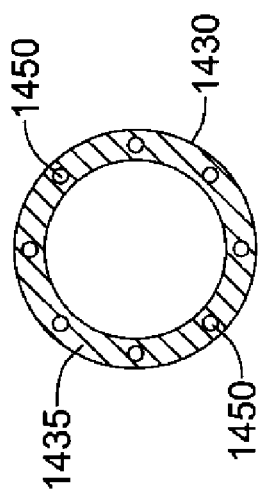

A portion of another illustrative embodiment of a perfusion member 1430 is depicted in FIG. 14. As shown in FIG. 14, a distal portion of the perfusion member 1430 proximate the distal end 1434 of the perfusion member 1430 may include a plurality of axial filaments 1450 extending along a length of the perfusion member 1430. In some embodiments, such as illustrated in FIG. 14A, the axial filaments 1450 may be embedded in the wall 1435 of the perfusion member 1430. However, in other embodiments, the axial filaments 1450 may be secured along either the inner or outer surface of the perfusion member 1430, if desired. In such instances, the axial filaments 1450 may be secured to the perfusion member 1430 by any suitable means, for example, solvent, heat or adhesive bonding. The axial orientation of the axial filaments 1450 provides the distal portion of the perfusion member 1430 with desired strength and rigidity, without compromising the ability of the perfusion member 1430 to be collapsed, folded and wrapped into a low profile around an elongate core member. The axial filaments 1450 may be formed of any suitable material. Some suitable materials include polymeric materials and metallic materials. Suitable polymeric materials include liquid crystal polymers, polyamide, polyester, polyvinylchloride, and polyethylene terephthalate, as well as other polymeric materials disclosed elsewhere herein, and the like. Suitable metallic materials include stainless steel, nickel-titanium alloys, tungsten, as well as other metallic materials disclosed elsewhere herein, and the like. In any case, some of all of the axial filaments 1450, or markers that are placed in the region of the axial filaments 1450, can be radiopaque and/or MRI compatible and/or MRI visible.

Figure 15A:
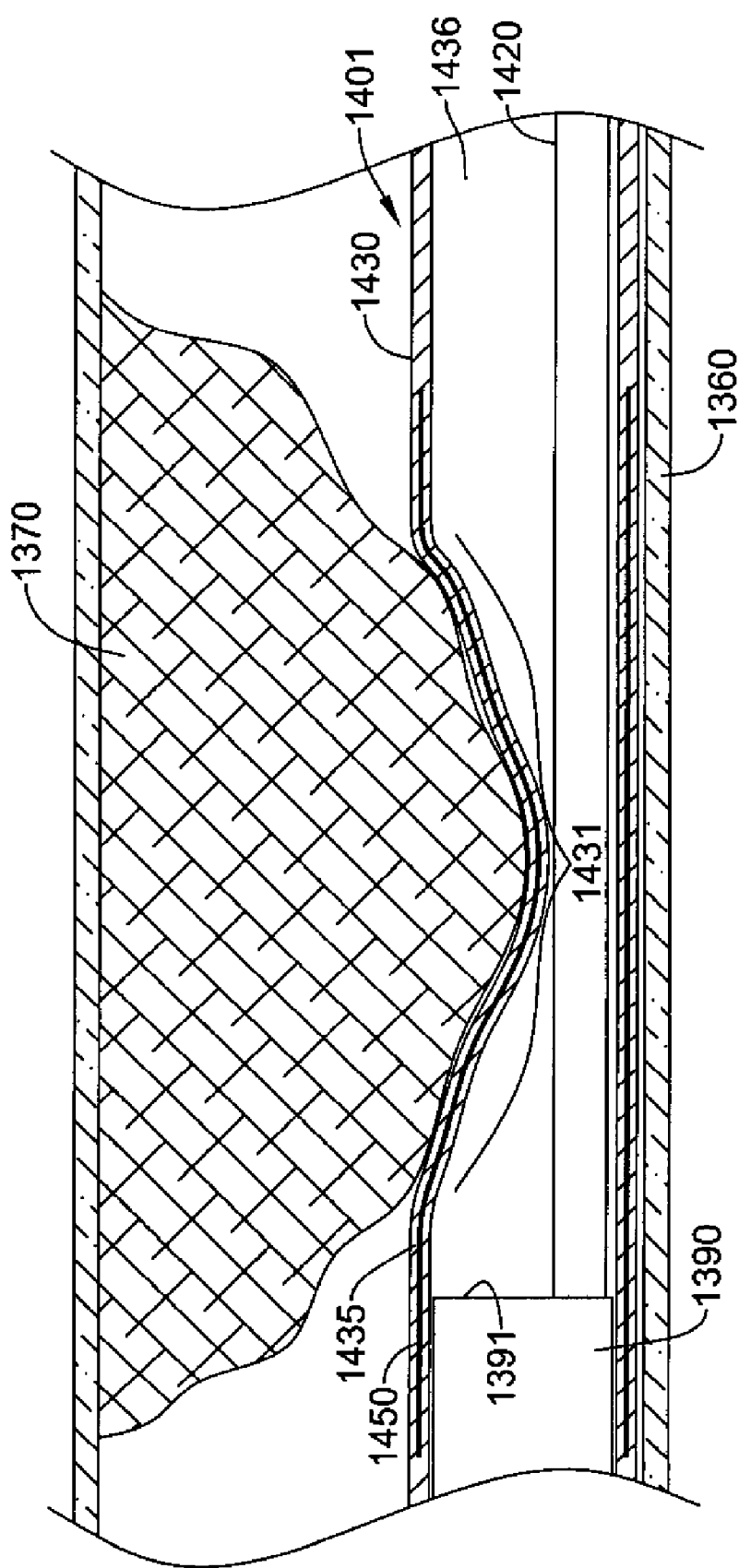
FIGS. 15A and 15B show an alternative method of using the perfusion member shown in FIGS. 14 and 14A.
Figure 15B:
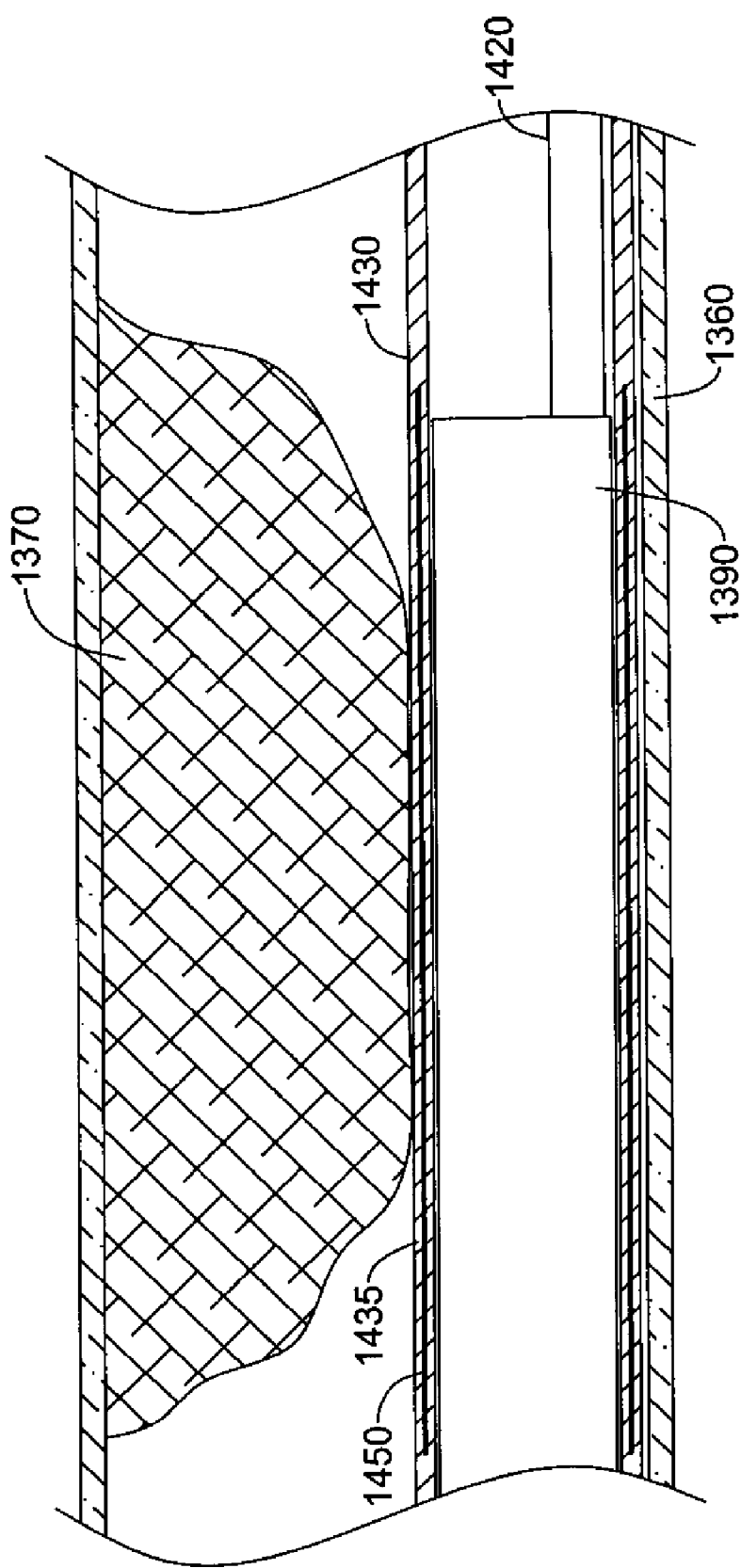

An exemplary method of using the illustrative perfusion member 1430 in conjunction with an elongate core member 1420, as a combination perfusion and occlusion device 1401, is depicted in FIGS. 15A-15B. The perfusion member 1430, as illustrated in FIG. 15A, has been expanded within the lumen of the vessel 1360 proximate an occlusion 1370. After initially being expanded, a constricted portion 1431 of the perfusion member 1430 may conform to the contour of the occlusion 1370 within the vessel 1360. The axial filaments 1450 may extend along the perfusion member 1430 through at least the constricted portion 1431 of the perfusion member 1430. The axial filaments 1450 may be sufficiently flexible such that the axial filaments 1450 may be readily curved through the constricted portion 1431 of the perfusion member 1430.

A medical device 1390, illustrated as a catheter, may be advanced through the lumen 1436 of the perfusion member 1430 to a location proximate the occlusion 1370. As the medical device 1390 approaches the occlusion 1370, the perfusion member 1430 may act as a "shoehorn" for the medical device 1390. That is, the perfusion member 1430 may facilitate passage of the medical device 1390 distally past the occlusion 1370 without adversely affecting the occlusion 1370 (e.g., dislodging and/or subjecting the occlusion 1370 to shear stresses). As the medical device 1390 approaches the constricted portion 1431 of the perfusion member 1430, resultant of the perfusion member's conformity around the occlusion 1370, the leading edge 1391 of the medical device 1390 may engage the wall 1435 of the perfusion member 1430. As the medical device 1390 is urged further distally, the leading edge 1391 of the medical device 1390 urges the wall 1435 radially outward, subjecting radially compressive forces upon the occlusion 1370. The axial filaments 1450 along the perfusion member 1430 may assist in radial compression of the occlusion 1370 and thus widening of the passage past the occlusion 1370, while guiding the medical device 1390 further distally through the lumen 1436.

FIG. 15B illustrates the medical device 1390 extending through the perfusion member 1430 to a location distal of the occlusion 1370. The occlusion 1370 is shown radially compressed toward the wall of the vessel 1360, yielding to the enlargement of the perfusion member 1430 as the medical device 1390 is passed therethrough. With the medical device 1390 positioned distal of the occlusion 1370, a further medical procedure may be performed in order to provide treatment, remove the occlusion 1370, or the like.

As mentioned above, the devices and methods shown in FIGS. 13A-15B can be used in conjunction with any of the devices and methods disclosed above. For example, the methods and devices shown in these figures can be used in facilitating the step of introducing a combination perfusion and occlusion device into a patient past an occlusion that is present in a patient's vasculature, and can also be used to introduce an additional medical device to a location of interest within a patient.

It is also contemplated that the embodiments described herein can be used to aspirate a target area in addition to, or rather than, perfusing a target area. In such a case, an occlusive member could be used to isolate an area or to prevent additional fluid flow through the area, and fluids could be suctioned out through an aspiration member, which can be any of the perfusion members described herein. In such cases, the distal end of the perfusion member of the embodiments described herein may be positioned proximal or distal of the occlusive member.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

We claim:

1. A combination perfusion and occlusion device comprising:
    an elongate shaft with proximal and distal ends;
    an occlusive member disposed on a distal portion of the elongate shaft, the occlusive member having a collapsed configuration and an expanded configuration, the occlusive member comprising material that is restrictive of blood flow;
    an elongate perfusion member disposed along at least a portion of the elongate shaft, the perfusion member having a collapsed configuration and an expanded configuration, the perfusion member defining a perfusion lumen in the expanded configuration, the perfusion member being disposed along the shaft from proximal the occlusive member to distal the occlusive member;
    wherein the occlusive member is a filter comprising a support hoop forming a filter opening and a filter material having pores extending distally from the support hoop to form a filter basket.

2. The device of claim 1, wherein the perfusion member is attached to the elongate shaft along at least a portion of the elongate shaft.

3. The device of claim 1, wherein the perfusion member is disposed along substantially the entire length of the elongate shaft.

4. The device of claim 1, wherein the perfusion member is disposed around the elongate shaft when the perfusion member is in its collapsed configuration.

5. The device of claim 1, wherein the perfusion member is eccentrically disposed along the elongate shaft when the perfusion member is in its expanded configuration.

6. The device of claim 1, wherein the perfusion member surrounds at least a portion of the occlusive member when the perfusion member is in its collapsed configuration.

7. The device of claim 1, wherein the perfusion member surrounds the entire occlusive member when the perfusion member is in its collapsed configuration.

8. The device of claim 1, wherein the occlusive member is eccentrically disposed along the elongate shaft.

9. The device of claim 1, wherein the occlusive member and the perfusion member are both eccentrically disposed along the elongate shaft.

10. The device of claim 1, wherein the occlusive member and the perfusion member are both eccentrically disposed on the elongate shaft.

11. The device of claim 1, wherein portions of the occlusive member and the perfusion member are in contact when they are in their expanded configurations.

12. The device of claim 1, wherein portions of the occlusive member and the perfusion member are attached to one another, and wherein the perfusion member and occlusive member together form a substantially circular cross-section.

13. The device of claim 1, wherein the perfusion member, when in its collapsed configuration, has a first longitudinal portion that is disposed around a portion of the elongate shaft and a second longitudinal portion that is disposed along side the elongate shaft, the first portion being distal of the second portion.

14. The device of claim 1, wherein the perfusion member, when in its collapsed configuration, wraps around the elongate shaft at least 540 degrees.

15. The device of claim 1, wherein the perfusion member comprises a seal in a distal portion of the perfusion member that has first and second configurations, the first configuration restricting fluid flow through the perfusion member and the second configuration allowing more fluid flow through the perfusion member than the fluid flow allowed by the first configuration, the seal having a pressure within the perfusion member at which it will move from the first to the second configurations.

16. The device of claim 15, wherein the seal is an adhesive that is disposed inside a sealed portion of the perfusion member, holding the sealed portion in a collapsed state, the adhesive releasing when the pressure is reached.

17. The device of claim 15, wherein the seal is a flap disposed in a distal portion of the perfusion member, the flap substantially sealing a lumen of the perfusion member, the flap opening when the pressure is reached.

18. The device of claim 1, further comprising a dilating member that is sized and shaped to be passed down a lumen of the perfusion member in order to form or enlarge the lumen.

19. The device of claim 1, wherein the perfusion member further comprises a hi-stable member along at least a portion of the perfusion member, the bi-stable member pre-disposed to assume one of a first and a second position, the first position placing the perfusion member in its collapsed configuration and the second position placing the perfusion member in its expanded configuration.

20. The device of claim 1, wherein the perfusion member and the elongate shaft are longitudinally translatable with respect to one another.

21. A combination perfusion and occlusion device comprising:
an elongate shaft with proximal and distal ends;
an occlusive member disposed on a distal portion of the elongate shaft, the occlusive member having a collapsed configuration and an expanded configuration, the occlusive member comprising material that is restrictive of blood flow;
an elongate perfusion member disposed along at least a portion of the elongate shaft, the perfusion member having a collapsed configuration and an expanded configuration, the perfusion member defining a perfusion lumen in the expanded configuration, wherein portions of the occlusive member and the perfusion member are in contact when they are in their expanded configurations;
wherein at least a portion of the perfusion member is disposed around at least a portion of the elongate shah when the perfusion member is in the collapsed configuration;
wherein the perfusion member is longitudinally translatable with respect to the elongate shaft; and
wherein the perfusion member and the occlusion member are both eccentrically disposed along the elongate shaft;
wherein the occlusive member is a filter comprising a support hoop forming a filter opening and a filter material having pores extending distally from the support hoop to form a filter basket.

22. The device of claim 21, wherein the perfusion member is of sufficient length to be disposed along substantially the entire length of the elongate shaft.

23. The device of claim 21, wherein the perfusion member is of sufficient length to be disposed along the shaft from proximal the occlusive member to distal the occlusive member.

24. The device of claim 21, wherein the perfusion member is disposed around the elongate shaft when the perfusion member is in its collapsed configuration.

25. The device of claim 21, wherein the perfusion member surrounds at least a portion of the occlusive member when the perfusion member is in its collapsed configuration.

26. The device of claim 21, wherein the perfusion member surrounds the entire occlusive member when the perfusion member is in its collapsed configuration.

27. The device of claim 21, wherein portions of the occlusive member and the perfusion member are attached to one another, and wherein the perfusion member and occlusive member together form a substantially circular cross-section.

28. The device of claim 21, wherein the perfusion member, when in its collapsed configuration, has a first longitudinal portion that is disposed around a portion of the elongate shaft and a second longitudinal portion that is disposed along side the elongate shaft, the first portion being distal of the second portion.

29. The device of claim 21, wherein the perfusion member, when in its collapsed configuration, wraps around the elongate shaft at least 540 degrees.

30. The device of claim 21, wherein the perfusion member comprises a seal in a distal portion of the perfusion member that has first and second configurations, the first configuration restricting fluid flow through the perfusion member and the second configuration allowing more fluid flow through the perfusion member than the fluid flow allowed by the first configuration, the seal having a pressure within the perfusion member at which it will move from the first to the second configurations.

31. The device of claim 30, wherein the seal is an adhesive that is disposed inside a sealed portion of the perfusion member, holding the sealed portion in a collapsed state, the adhesive releasing when the pressure is reached.

32. The device of claim 30, wherein the seal is a flap disposed in a distal portion of the perfusion member, the flap substantially sealing a lumen of the perfusion member, the flap opening when the pressure is reached.

33. The device of claim 21, further comprising a dilating member that is sized and shaped to be passed down a lumen of the perfusion member in order to form or enlarge the lumen.

34. The device of claim 21, wherein the perfusion member further comprises a bi-stable member along at least a portion of the perfusion member, the bi-stable member pre-disposed to assume one of a first and a second position, the first position placing the perfusion member in its collapsed configuration and the second position placing the perfusion member in its expanded configuration.

* * * * *